United States Patent
Kotani et al.

[11] Patent Number: 5,121,050
[45] Date of Patent: Jun. 9, 1992

[54] METHOD OF MEASURING PHYSICAL PROPERTIES BY SUPER-THIN LIQUID MEMBRANE FORMING MODE AND INTERFACE REACTION DETECTION TYPE BOISENSOR BY SUPER-THIN LIQUID MEMBRANE FORMING MODE

[75] Inventors: Haruo Kotani; Katsuhiko Tomita; Junji Kojima; Takeshi Kohno, all of Miyanohigashi, Japan

[73] Assignee: Horiba, Ltd., Kyoto, Japan

[21] Appl. No.: 464,601

[22] Filed: Jan. 12, 1990

Related U.S. Application Data

[63] Continuation of Ser. No. 212,978, Jun. 29, 1988, abandoned.

[30] Foreign Application Priority Data

Jul. 4, 1987 [JP] Japan ................... 62-168377
Jul. 6, 1987 [JP] Japan ................... 62-169198

[51] Int. Cl.⁵ .......................... G01N 27/00
[52] U.S. Cl. .......................... 324/71.5; 324/439
[58] Field of Search .......... 324/71.5, 692, 697, 324/715, 724, 438, 439, 450, 444; 204/409, 411

[56] References Cited

U.S. PATENT DOCUMENTS

| | | | |
|---|---|---|---|
| 2,925,370 | 2/1960 | Rohrer | 204/435 |
| 3,434,953 | 3/1969 | Porter et al. | 204/408 |
| 3,528,287 | 9/1970 | Melcher | 324/439 X |
| 4,123,701 | 10/1978 | Josefsen et al. | 324/692 X |
| 4,439,526 | 3/1984 | Columbus | 204/409 X |
| 4,529,495 | 7/1985 | Marsoner | 204/411 |
| 4,713,347 | 12/1987 | Mitchell et al. | 324/439 X |
| 4,777,019 | 10/1988 | Dandekar | 324/71.5 X |
| 4,797,188 | 1/1989 | Tomita | 204/414 |
| 4,816,132 | 3/1989 | Kotani et al. | 204/408 |
| 4,902,399 | 2/1990 | Durley, III et al. | 204/409 |
| 4,911,794 | 3/1991 | Parce et al. | 204/409 X |

Primary Examiner—Kenneth A. Wieder
Attorney, Agent, or Firm—Price, Gess & Ubell

[57] ABSTRACT

The present invention is characterized by a solid body disposed so that a remarkably small gap may be formed between it and a surface of an electrode. A super-thin liquid membrane is formed in the small gap by an interfacial tension of a liquid. An object to be measured is applied to or acted upon either the solid body or the super-thin liquid membrane. An electric signal due to the physical properties of the super-thin liquid membrane itself or an electric signal due to a chemical or physical reaction, which is generated on an interface of the solid body and the super-thin liquid membrane and diffused through the super-thin liquid membrane itself, is detected by means of the electrode to measure the physical properties of the object to be measured.

19 Claims, 17 Drawing Sheets

METHOD OF MEASURING PHYSICAL PROPERTIES BY SUPER-THIN LIQUID MEMBRANE FORMING MODE AND INTERFACE REACTION DETECTION TYPE BOISENSOR BY SUPER-THIN LIQUID MEMBRANE FORMING MODE

This is a continuation of application Ser. No. 212,978, filed on Jun. 29, 1988, now abandoned, for a METHOD OF MEASURING PHYSICAL PROPERTIES BY SUPER-THIN LIQUID MEMBRANE FORMING MODE AND INTERFACE REACTION DETECTION TYPE BOISENSOR BY SUPER-THIN LIQUID MEMBRANE FORMING MODE.

BACKGROUND OF THE INVENTION

1. Field of the Invention

The present invention relates to a quite novel method of measuring physical properties by a super-thin liquid membrane forming mode and a quite novel interface reaction detection type biosensor by a super-thin liquid membrane forming mode applicable regardless of whether it is a solid, liquid or gaseous object to be measured.

2. Description of the Prior Art

The following methods and the like have been known as a method of measuring physical properties using a small quantity of sample:

(1) A flow-through type method as shown in FIG. 20(A). A liquid sample c, as an object to be measured, is introduced at an appointed quantity and followed by another appointed quantity into a capillary b provided with a sample electrode a therein, the electrode being a single-type measuring or reference electrode, or complex-type measuring and reference electrode.

(2) A drop type method as shown in FIG. 20(B). An appointed quantity of liquid sample c, as an object to be measured, is introduced drop by drop by means of a micropipette (not shown) into a sample-introducing concave portion d provided with a sample electrode a in a bottom portion thereof.

(3) A method as shown in FIG. 20(C). An absorption member e impregnated with a liquid sample c, as an object to be measured, is placed on a sample electrode a in a closely contacting relation.

However, all of the above-described various methods (1), (2), (3) are the direct measuring method for the liquid sample c as the object to be measured. Consequently, the measurement is very difficult or impossible according to the items to be measured.

Horiba, Ltd. has developed measuring methods suitable for such cases, that is, indirect measuring methods (4) by a so-called reaction detecting mode or a living body reaction detecting mode, in which the liquid sample c, as the object to be measured, is brought into contact with a solid reactive substance to thereby cause a chemical or physical reaction between them and an electrical change due to the reaction is detected by the sample electrode. Alternatively, the liquid sample c is brought into contact with a membrane fixedly carrying a living body reactive substance acting upon a living body thereon to cause a living body reaction between them and an electrical change due to the reaction is detected by the sample electrode. Not only these measuring methods, but also the biosensor for carrying out the methods have been applied for patent in Japan (see, for example, Japanese patent application No. 3152193/1986).

In addition, the above-described reactive substance or membrane includes, for example, an enzyme-fixed membrane and an antibody-fixed membrane.

According to the indirect measuring method by a reaction detecting mode (4), as shown in FIG. 21, a solid reactive substance g (for example, an enzyme-fixed membrane) is placed on the sample electrode a (for example, a hydrogen peroxide electrode consisting of a platinum electrode and a silver electrode and the like). A buffer solution layer f having an appointed thickness is disposed between the solid reactive substance g and the sample electrode a. An appointed quantity of a liquid sample c, as the object to be measured, is introduced on the solid reactive substance g drop by drop by means of a micropipette h and the like to detect an electrical change due to a chemical or physical reaction by means of the electrode a. The electrical change is produced on an interface between the liquid sample c and the solid reactive substance g, the reaction spreads into the solid reactive substance g, and finally diffuses into the buffer solution layer f, whereby measuring physical properties of the object is accomplished.

In addition, with a biosensor, to which the indirect measuring method (4) by the living body reaction detecting mode is applied, as shown in FIG. 22, a living body reactive membrane g' (for example, an enzyme-fixed membrane) is placed on a sample electrode a (for example, a hydrogen peroxide electrode consisting of a platinum electrode and a silver electrode and the like). A buffer solution layer f having an appointed thickness is disposed between the living body reactive membrane g' and the sample electrode a. An appointed quantity of a sample solution c, as the object to be measured, is introduced on the living body reactive membrane g' drop by drop by means of a micropipette h and the like to detect an electrical change due to a living body reaction by means of the electrode a. The electrical change is produced on an interface between the sample solution c and the living body reactive membrane g'. The reaction then spreads into the living body reactive membrane g', and finally diffuses into the buffer solution layer f, whereby measuring physical properties of the object is accomplished.

However, the measuring methods using a small quantity of sample according to the above-described conventional art and prior art have also shown the following kinds of problems:

(a) An object to be measured must be liquid. Accordingly, in the case where physical properties of solids and gases are to be measured, the solids and gases are first dissolved in an appointed quantity of liquid, such as pure water, which does not have an effect upon the physical properties, to form a liquid sample. That is to say, pretreatment is required, which makes the measurement remarkably troublesome.

(b) Only a small quantity of the liquid sample c, as the object to be measured, is required. But in order to achieve a highly accurate measurement, at least about 0.2 to 0.5 ml of the sample liquid is required for one measurement. In particular, in the case of the above-described indirect measuring method by the reaction detecting mode, a comparatively large amount of liquid sample c is required so that the reaction can be sufficiently spread into the solid reactive substance g. Accordingly, it has been desirable to develop an art capable of achieving a highly accurate measurement using a still smaller amount of sample. In addition, the measurement by means of the electrode a is impossible until the chemical or physical reaction produced on an interface between the liquid sample c, as the object to be measured, and the solid reactive substance g spreads into the solid reactive substance g itself, diffuses into the buffer solution layer f and reaches the electrode a. In short, the reaction is indirectly detected through the reactive substance g itself, which is solid, and the buffer solution layer f for transmitting the reaction. Thus, the reaction-diffusing time is remarkably increased and a sufficiently large stationary detection signal is remarkably difficult to obtain and further, the thickness of the buffer solution layer f is remarkably difficult to control.

In addition, the biosensors according to the above-described prior art have exhibited the problems similar to those in the above-described (b).

SUMMARY OF THE INVENTION

The present invention was achieved in view of the above-described actual state of matters, and it is an object of the present invention to provide a method of measuring physical properties by a super-thin liquid membrane forming mode capable of accurately measuring the physical properties of an object to be measured by an easy operation in a short time regardless of whether the object to be measured is solid, liquid or gaseous, even in the case where a remarkably small amount of sample can be used. An object is also to provide such measurement by an interface reaction detection type biosensor by a super-thin liquid membrane forming mode capable of accurately measuring the physical properties of the object to be measured by an easy operation in a short time, even in the case where a remarkably small amount of sample can be used.

In order to achieve the above-described objects, the method of measuring physical properties by a super-thin liquid membrane forming mode according to the present invention is shown in a general diagrammatical longitudinal, sectional view of FIG. 1(A) and a partially enlarged view of FIG. 1(B). The present invention is characterized by a solid body A disposed so that a remarkably small gap C may be formed between it and surfaces of electrodes B and $B^1$. As can be appreciated, the respectable electrodes B and $B^1$ can be a single-type measuring, or a reference electrode, or a complex-type measuring and reference electrode. A super-thin liquid membrane D is formed in the small gap C by an interfacial tension of a liquid. An object to be measured is applied to or acted upon either the solid body A or the super-thin liquid membrane D. An electric signal due to the physical properties of the super-thin liquid membrane D itself or an electric signal due to a chemical or physical reaction, which is generated on an interface of the solid body A and the super-thin liquid membrane D and diffused through the super-thin liquid membrane D itself, is detected by means of the electrode B to measure the physical properties of the object to be measured as shown in FIG. 1(A) a measuring electrode B and a reference electrode $B^1$ can be connected to an amplifier to provide an output indicative of the measured sample.

The following effects can be exhibited by the adoption of such measurement.

As is more obvious from the preferred embodiments, which will be mentioned later, with a method of measuring physical properties by a super-thin liquid membrane forming mode according to the present invention, the physical properties of the object to be measured can be accurately and directly measured regardless of whether the object to be measured is a liquid, solid or gas. The measurement can be accomplished without requiring a troublesome pretreatment of first liquefying the object to be measured by suitably selecting the combination of substances applied to each element, such as the solid body A, the super-thin liquid membrane D, a substance E to be acted upon the super-thin liquid membrane through the solid body A constructed so as to be permeable to liquids or gases or the like from the combinations roughly shown in the following Table:

| Object to be Measured | Combination of Substances to be Applied to Respective Elements | | |
|---|---|---|---|
| | Acting Substance | Solid Body | Super-Thin Liquid Membrane |
| Liquid | | Nonreactive substance | Liquid object to be measured |
| Liquid | | Reactive substance | Liquid object to be measured |
| Solid | | Solid object to be measured | Liquid reactive substance |
| Liquid | Liquid reactive substance | Liquid-Permeable nonreactive substance | Liquid object to be measured |
| Liquid | Liquid object to be measured | Liquid-permeable nonreactive substance | Liquid reactive substance |
| Liquid | Gaseous reactive substance | Gas-permeable nonreactive substance | Liquid object to be measured |
| Gas | Gaseous object to be measured | Gas-permeable nonreactive substance | Liquid reactive substance |
| Solid | Liquid reactive substance | Liquid-permeable nonreactive substance | Liquid reactive substance + super-thin liquid memebrane solid (or powdery) object to be measured |
| Solid | Liquid reactive substance | Nonreactive substance oozing out liquid reactive substance | Liquid reactive substance + super-thin liquid membrane solid (or powdery) object to be measured |

In addition, in the case where any one of the above-described combinations is adopted as the substances to be applied to the solid body A, super-thin liquid membrane D, acting substance E and the like, the super-thin liquid membrane D is formed within the remarkably small gap C between the solid body A and the surface of the electrode B. An electric signal, due to the physical properties of the super-thin liquid membrane D itself or an electric signal due to the chemical or physical reaction generated on the interface of the solid body A and the super-thin liquid membrane D and diffused through the super-thin liquid membrane D itself, as schematically shown by a dotted arrow in FIG. 1(B), is directly detected by means of the electrode. Thereby, the physical properties of a remarkably small amount of the sample (in the case of liquid, several microliters) in comparison with the amount of the sample used in the methods (1) to (4) according to said conventional and prior art can be accurately measured. The reaction diffusing time through the super-thin liquid membrane D is remarkably short so that the physical properties of the object to be measured can be efficiently measured within a remarkably short time. There is a tendency that the sensitivity of measurement and response speed are improved with a decrease in thickness of this super-thin liquid membrane D.

In addition, a moderate super-thin liquid membrane D can be automatically formed by effectively utilizing an interfacial tension of the liquid, so that the super-thin liquid membrane D can be formed by a remarkably easy operation.

The interface reaction detection type biosensor by a super-thin liquid membrane forming mode according to the present invention is shown in a partially enlarged view in FIG. 13. It is characterized by a living body reacting membrane A' showing a living body reaction upon a solution O to be measured. The electrode B is arranged to be substantially brought into close contact to the membrane A' or capable of being brought into close contact to each other, and the super-thin liquid membrane D of the solution O to be measured can be disposed within the remarkably small gap C formed between the living body reacting membrane A' and the electrode B utilizing the interfacial tension of the solution O to be measured.

Such characteristic construction exhibits the following operation.

That is to say, with the interface reaction detection type biosensor by a super-thin liquid membrane forming mode according to the present invention, as more obvious from the various kinds of preferred embodiments which will be mentioned later, the super-thin liquid membrane D of the solution O to be measured is formed within the remarkably small gap C between the living body reacting membrane A' and the surface of the electrode B. The electric signal, due to the living body reaction generated on the interface of the living body reacting membrane A' and the super-thin liquid membrane D and diffused through the super-thin liquid membrane D itself, is directly detected by means of the electrode B, as schematically shown by an arrow in FIG. 13. Thus, the physical properties of a remarkably small amount of sample (about several microliters) in comparison with the amount of sample used in the above methods (1) to (4) according to the conventional and prior art can be accurately measured. The reaction diffusing time through the super-thin liquid membrane D is remarkably short so that the physical properties of the solution O to be measured can be efficiently measured within a remarkably short time. There is a tendency that the sensitivity of measurement and response speed are improved with a decrease in thickness of this super-thin liquid membrane D.

In addition, a moderate super-thin liquid membrane D can be automatically formed by effectively utilizing an interfacial tension of the solution O to be measured so that the measuring operation is very easy.

BRIEF DESCRIPTION OF THE DRAWINGS

In addition, FIGS. 2 to 12 are the drawings for describing various preferred embodiments of a method according to the present invention, in which:

FIG. 8(A) and FIG. 7(B) are a general diagrammatical longitudinal, sectional view and a partially enlarged view thereof, respectively, showing a seventh preferred embodiment;

Figure 14:
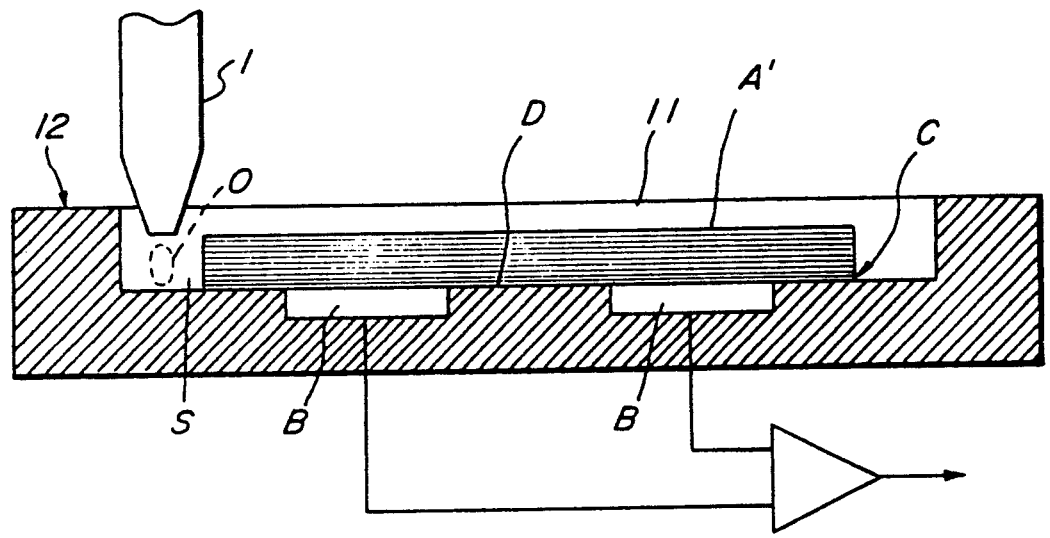
Figure 15:
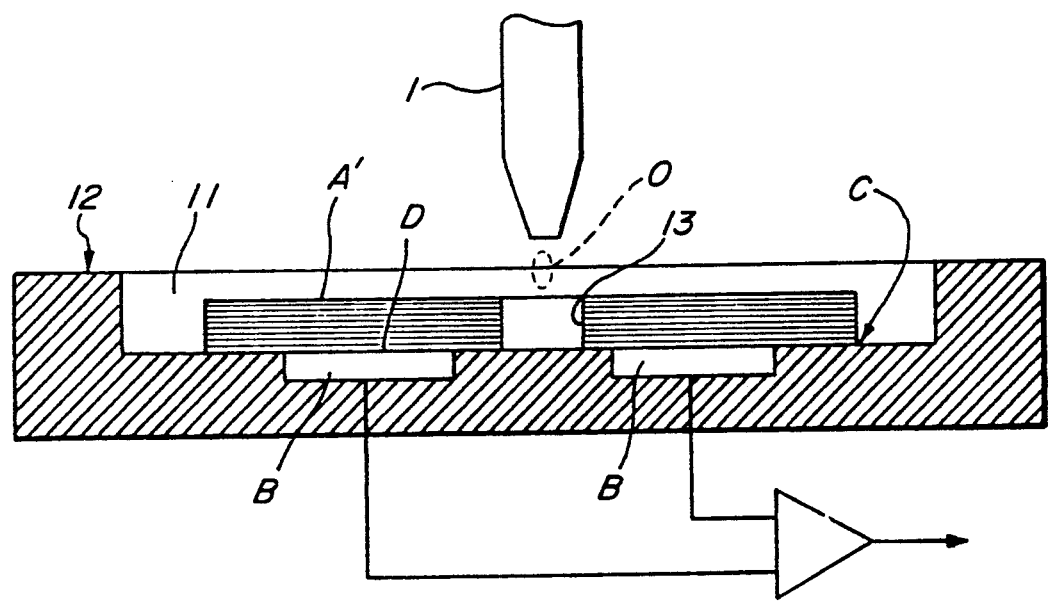
Figure 16:
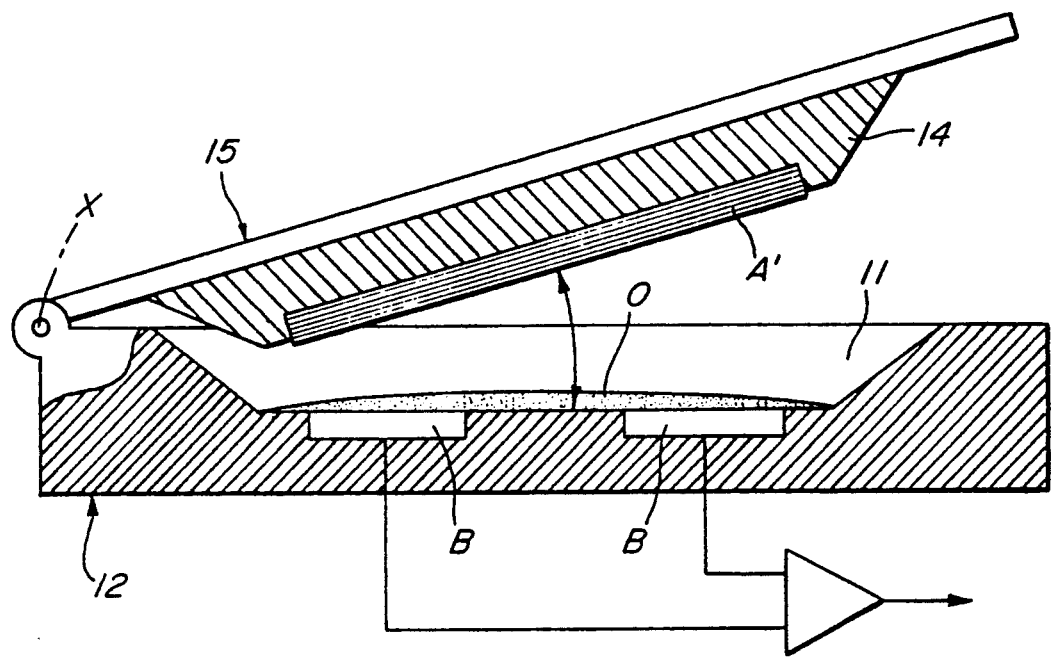
Figure 17:
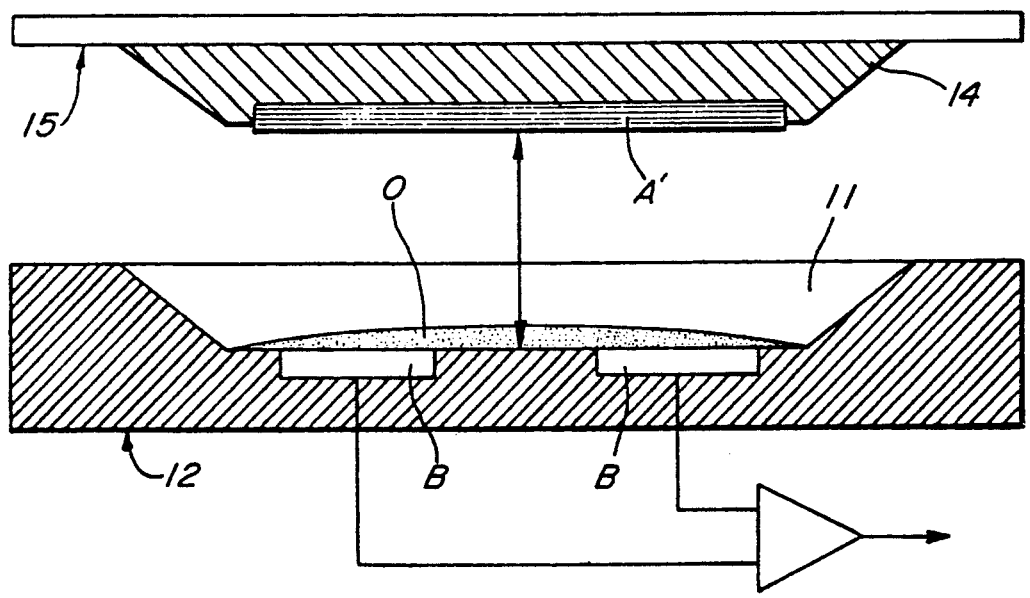
Figure 18:
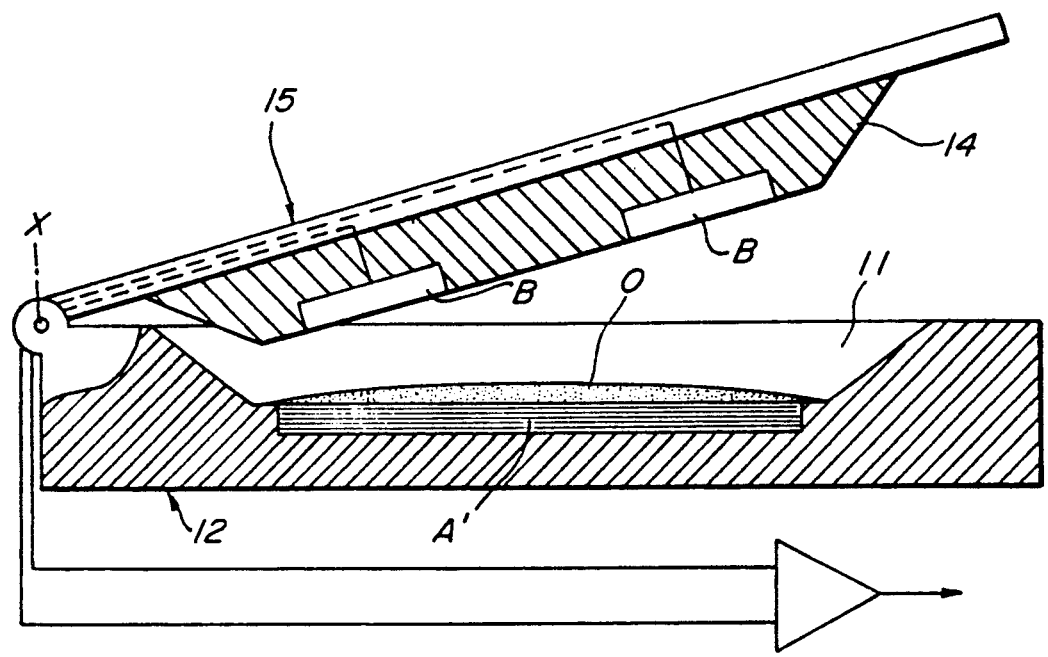
Figure 19:
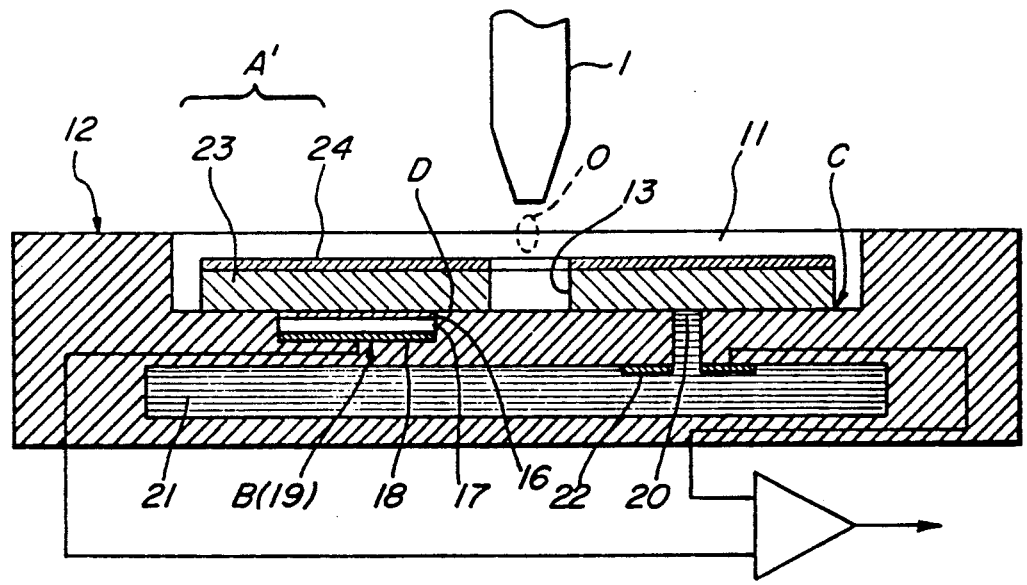

In addition, various kinds of preferred embodiments of the present invention are described in FIGS. 14 to 19, in which:

FIG. 14 is a general diagrammatical longitudinal, sectional view showing a twelfth preferred embodiment;

FIG. 15 is a general diagrammatical longitudinal, sectional view showing a thirteenth preferred embodiment;

FIG. 16 is a general diagrammatical longitudinal, sectional view showing a fourteenth preferred embodiment;

FIG. 17 is a general diagrammatical longitudinal, sectional view showing a fifteenth preferred embodiment;

FIG. 18 is a general diagrammatical longitudinal sectional view showing a sixteenth preferred embodiment; and FIG. 19 is a general diagrammatical longitudinal, sectional view showing a specific application example of the present invention.

Figure 20A:
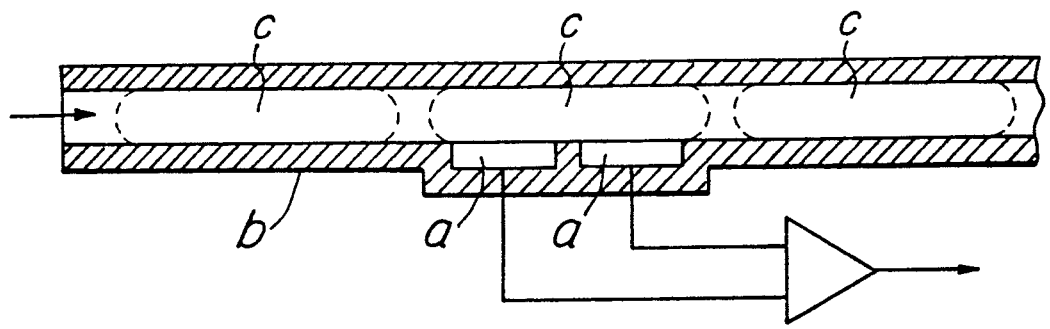
Figure 20B:
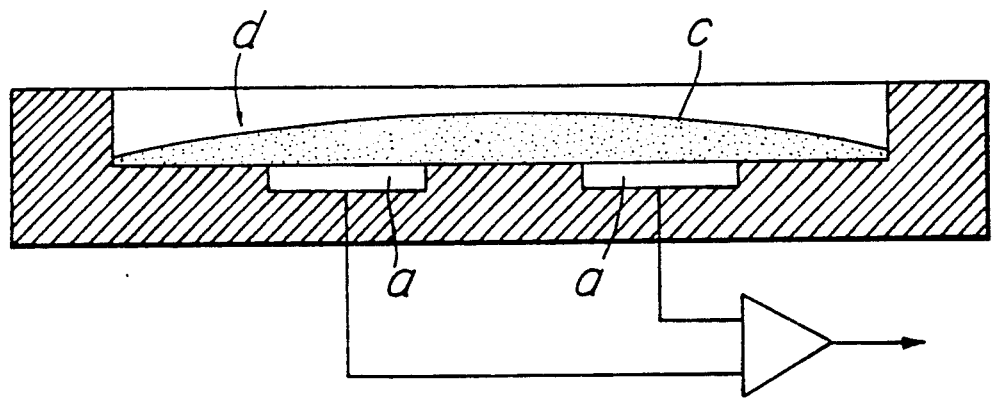
Figure 20C:
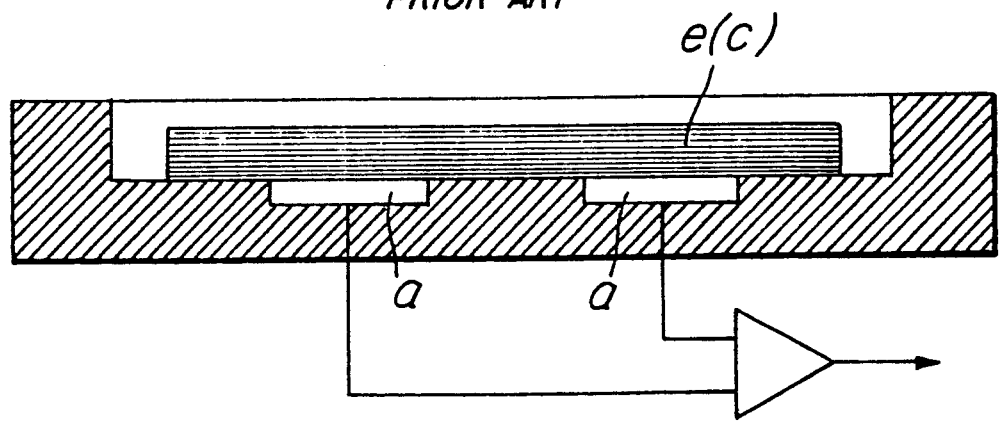
Figure 21:
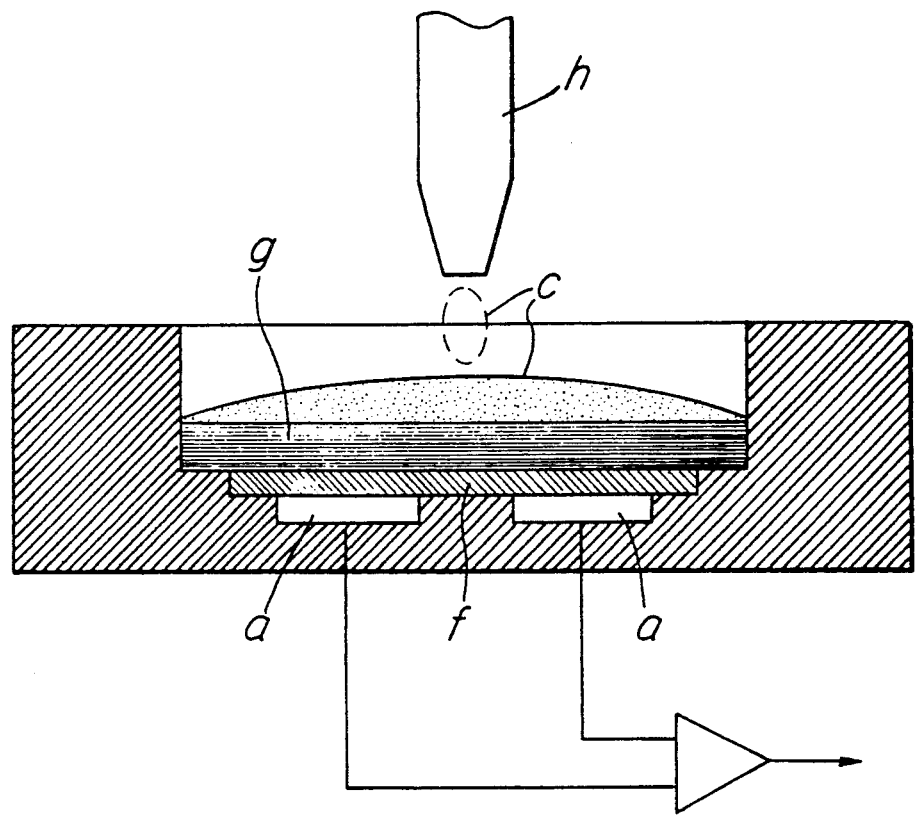
Figure 22:
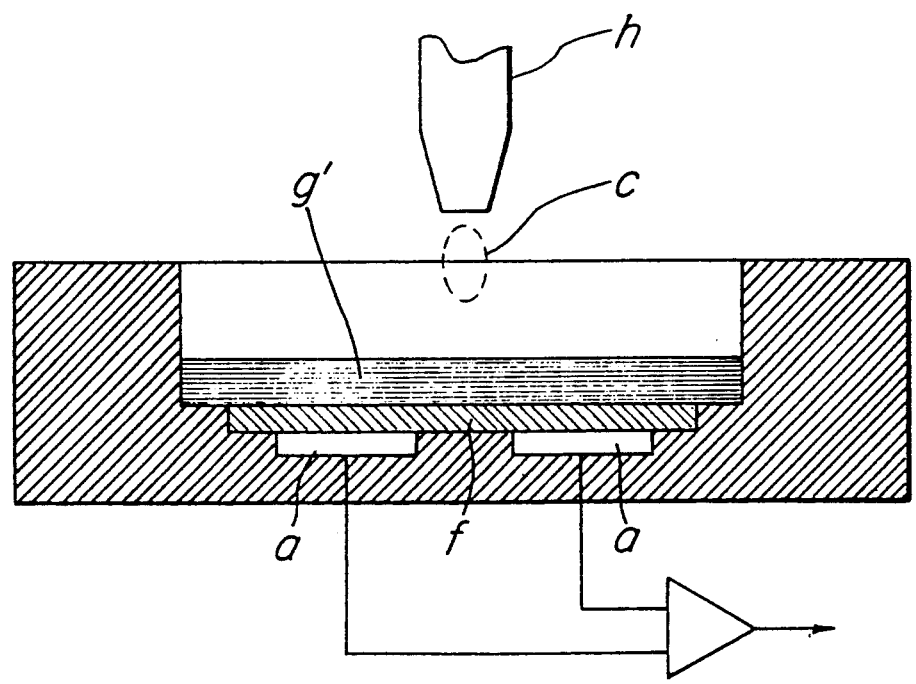

Also, the background of the present invention and the points of problem of the conventional and prior art are described with reference to FIGS. 20 to 22, in which:

FIG. 20(A) FIG. 20(B) and FIG. 20(C) are diagrams showing a method using a small amount of sample according to the conventional art; and FIGS. 21, 22 are diagrams showing a method using a small amount of sample according to the prior art.

DESCRIPTION OF THE PREFERRED EMBODIMENTS

The preferred embodiments of the present invention will be described below with reference to FIGS. 2 to 12 and FIGS. 14 to 19.

At first, a method of measuring physical properties by a super-thin liquid membrane forming mode, which is a first embodiment of the present invention, is described.

FIRST EXAMPLE

Figure 1A:
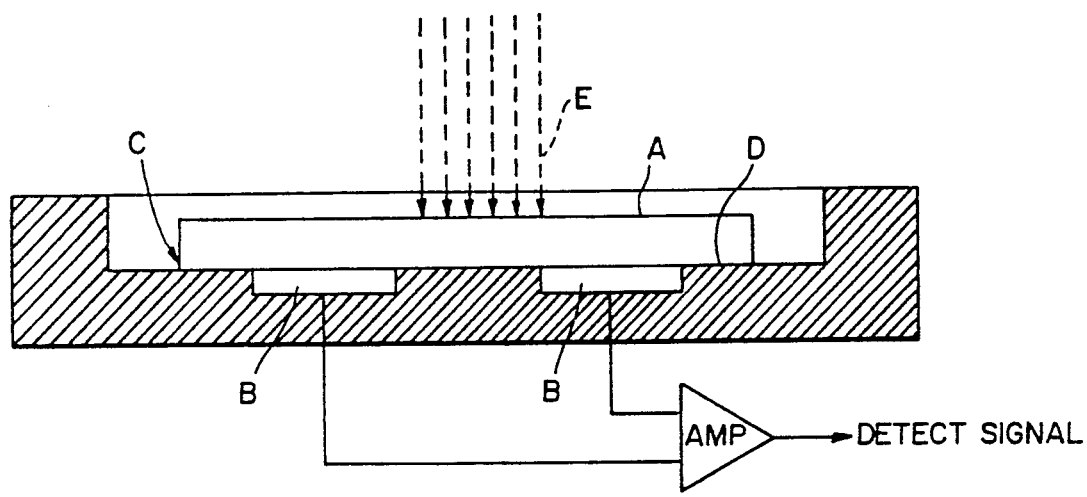
FIG. 1(A) and FIG. 1(B) are a general diagrammatical longitudinal, sectional view and a partially enlarged view thereof, respectively, for describing the inclusive method of measuring physical properties by a super-thin liquid membrane forming mode according to the present invention.
Figure 1B:
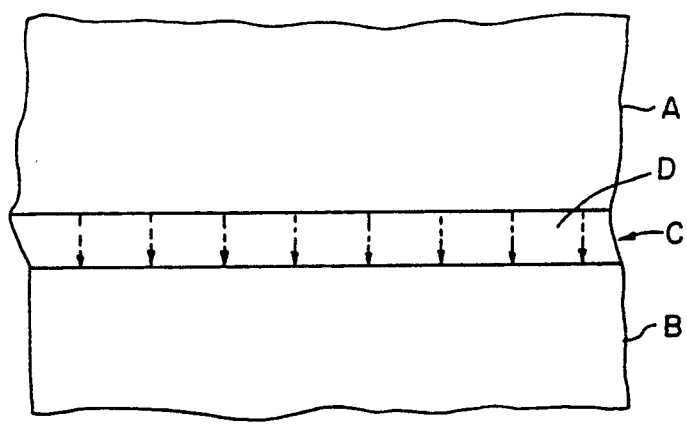
Figure 2A:
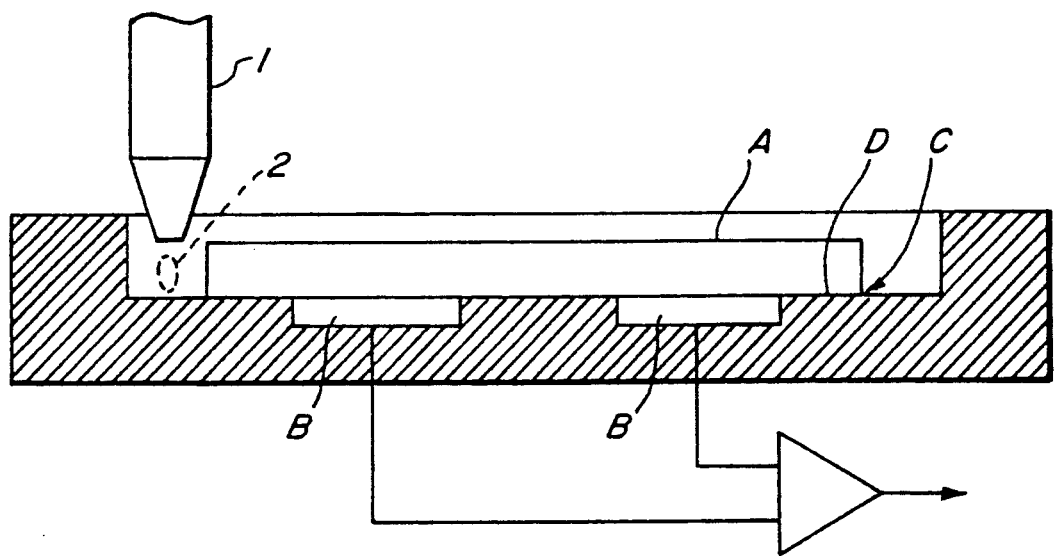
FIG. 2(A) and FIG. 2(B) are a general diagrammatical longitudinal, sectional view and a partially enlarged view thereof, respectively, showing a first preferred embodiment.
Figure 2B:
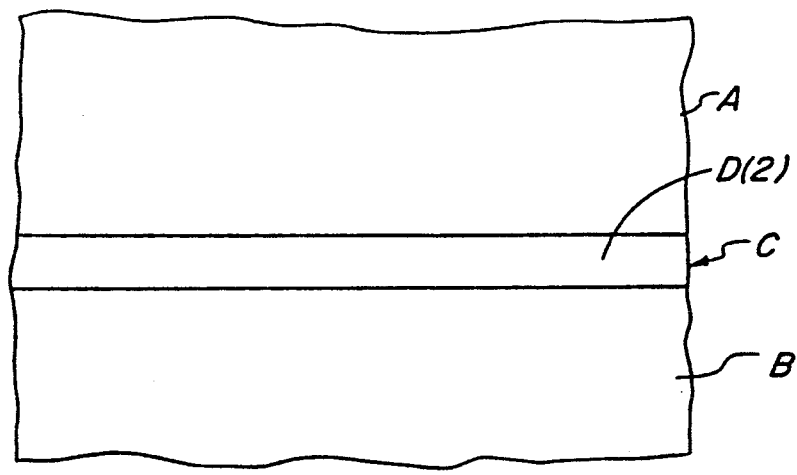

At first, as shown in FIG. 2(A), (B), the solid body A formed of a substance, which does not chemically or physically act upon the object to be measured (liquid object in this case), is disposed on the surface of the electrodes B, $B^1$ (for example, an electrode B for use in the measurement of ion-concentration, reference electrode $B^1$ and the like). It is so disposed, for example, by merely its weight or placing it on the surface of the electrodes B, $B^1$ and then pressing by some force so as to be substantially brought into close contact with the surface of the electrodes B, $B^1$. Then, the liquid object 2 to be measured is given drop by drop (a remarkably small amount, such as several microliters, is sufficient) to the vicinity of the circumferential portion of a contact surface between the solid body A and the surface of the electrodes B, $B^1$ by means of, for example, a micropipette 1 and the like. The liquid object 2 to be measured is oozed and diffused all over the remarkably small gap C formed between the solid body A and the surface of the electrode B, $B^1$ to dispose a super-thin liquid membrane between the solid body A and the surface of the electrodes B, $B^1$. Detecting an electric signal due to the physical property of the liquid object 2 to be measured by means of the electrodes B, $B^1$ to measure the physical property (ion-concentration in this case) of the liquid object 2 is accomplished.

In addition, although in the above-described first preferred embodiment, to dispose the super-thin liquid membrane D formed of the liquid object 2 to be measured in the remarkably small gap C formed between the solid body A and the surface of the electrodes B, B, the solid body A was first positioned so as to be substantially brought into close contact with the surface of the electrodes B, $B^1$ and then the liquid object 2 to be measured was given drop by drop to the vicinity of the circumferential portion of the contact surface between the solid body A and the surface of the electrodes B, $B^1$ so as to be oozed and diffused all over the remarkably small gap C by the interfacial tension thereof, this first preferred embodiment may be modified as follows:

At first, the liquid object 2 to be measured may be given drop by drop onto the surface of the electrodes B, $B^1$ by means of the micropipette 1 and the like. Then, the solid body A is disposed on the surface of the electrodes B, $B^1$ so as to be substantially brought into close contact with the surface of the electrodes B, $B^1$ with the given liquid object 2 to be measured between the solid body A and the surface of the electrodes B, $B^1$. This is done by merely placing the solid body A on the surface of the electrodes B, B or placing the solid body A on the surface of the electrodes B, $B^1$ and then applying some pressing force and the like. This diffuses the liquid object 2 to be measured all over the remarkably small gap C formed between the solid body A and the surface of the electrodes B, $B^1$.

SECOND EXAMPLE

Figure 3A:
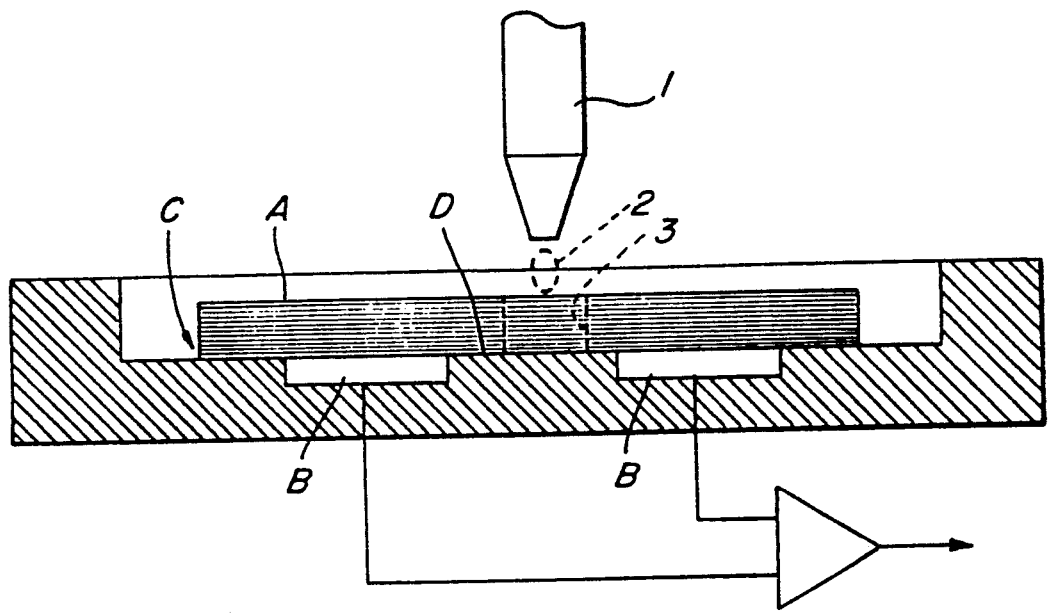
FIG. 3(A) and FIG. 3(B) are a general diagrammatical longitudinal, sectional view and a partially enlarged view thereof, respectively, showing a second preferred embodiment.
Figure 3B:
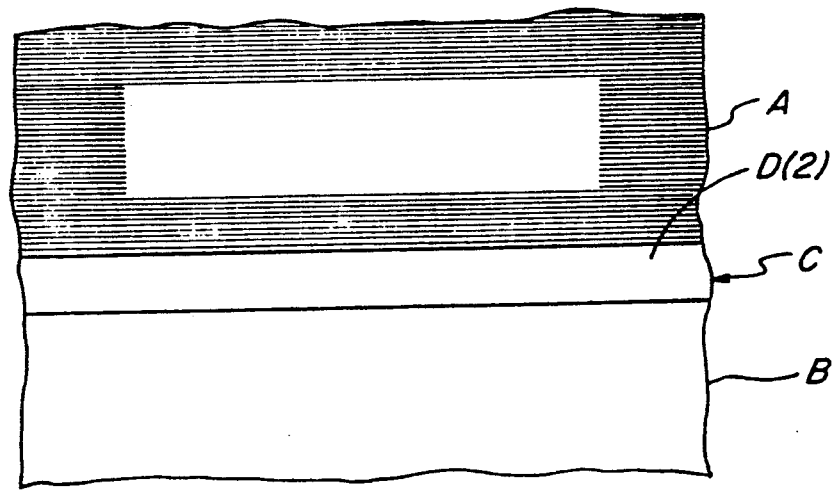

As shown in FIG. 3(A), (B), a solid body A, provided with through holes 3 or composed of a porous body and the like, so that a liquid object 2 to be measured can be transmitted or passed therethrough, is formed of a material which does not chemically or physically act upon the liquid object 2 to be measured. At first, the solid body A is positioned so as to be substantially brought into close contact with a surface of electrodes B, $B^1$ and then the liquid object 2 to be measured is given drop by drop onto a surface of the solid body A by means of a micropipette 1 and the like. This transmits or passes the given liquid object 2 to be measured through the solid body A and diffuses the liquid object 2 to be measured all over a remarkably small gap C formed between the solid body A and the surface of the electrodes B, $B^1$ by an interfacial tension thereof. Disposing a super-thin liquid membrane D between the solid body A and the surface of the electrodes B, $B^1$ enables detection of an electric signal due to a physical property of the object to be measured, which itself composes the super-thin liquid membrane D, and thus measurement of the physical property of the liquid object 2 to be measured is accomplished.

THIRD EXAMPLE

Figure 4A:
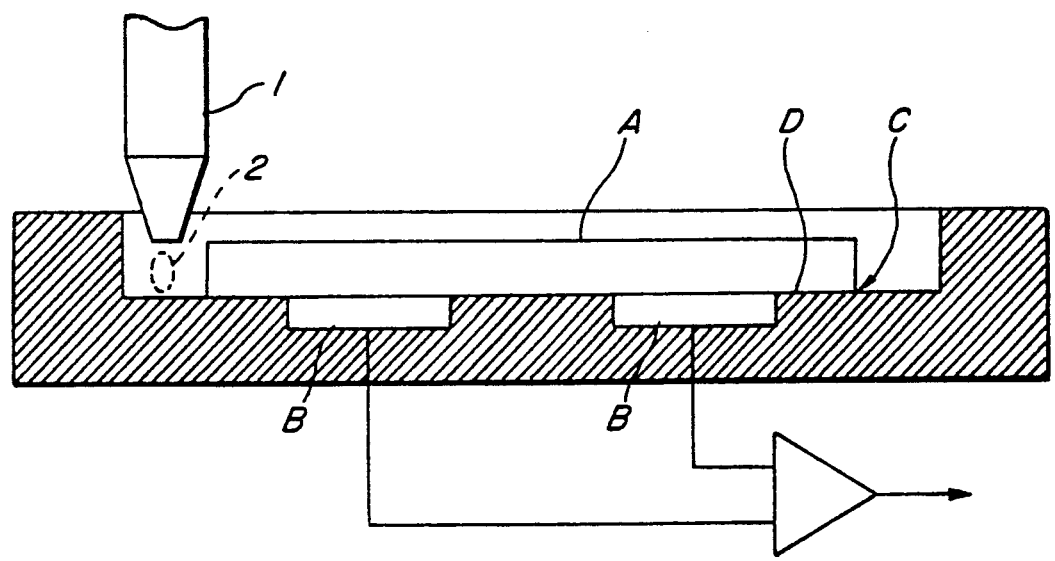
FIG. 4(A) and FIG. 4(B) are a general diagrammatical longitudinal, sectional view and a partially enlarged view thereof, respectively, showing a third preferred embodiment.
Figure 4B:
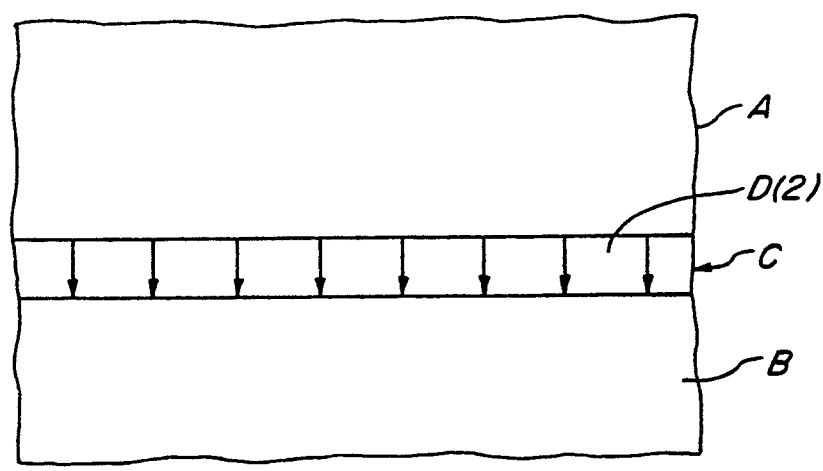

As shown in FIG. 4(A), (B), a solid body A, which is formed of a material that chemically or physically acts upon a liquid object 2 to be measured, is used. At first, the solid body A is positioned so as to be substantially brought into close contact with a surface of electrodes B, $B^1$. The liquid object 2 to be measured is then given drop by drop onto the vicinity of a circumferential portion of a contact surface between the solid body A and the surface of the electrodes B, $B^1$ by means of a micropipette 1 and the like. This transmits and diffuses the liquid object 2 to be measured all over a remarkably small gap C formed between the solid body A and the surface of the electrodes B, $B^1$. Disposing a super-thin liquid membrane D between the solid body A and the surface of the electrodes B, $B^1$ in the same manner as in the first EXAMPLE is provided to detect an electric signal due to a chemical or physical reaction, which is generated by a mutual action of a reactive substance composing the solid body A and the liquid object 2 composing the super-thin liquid membrane D. The reaction is on an interface between the solid body A and the super-thin liquid membrane D and the reaction is diffused through the super-thin liquid membrane D itself. The electric signal is measured by means of the electrodes B, $B^1$, which is a measurement of the physical property of the liquid object 2 to be measured, as shown in FIG. 4(A), (b).

Also in this third EXAMPLE, in order to dispose the super-thin liquid membrane D formed of the liquid object 2 to be measured within the remarkably small gap C formed between the solid body A and the surface of the electrodes B, $B^1$, the same modification as in said first EXAMPLE may be adopted.

FOURTH EXAMPLE

Figure 5A:
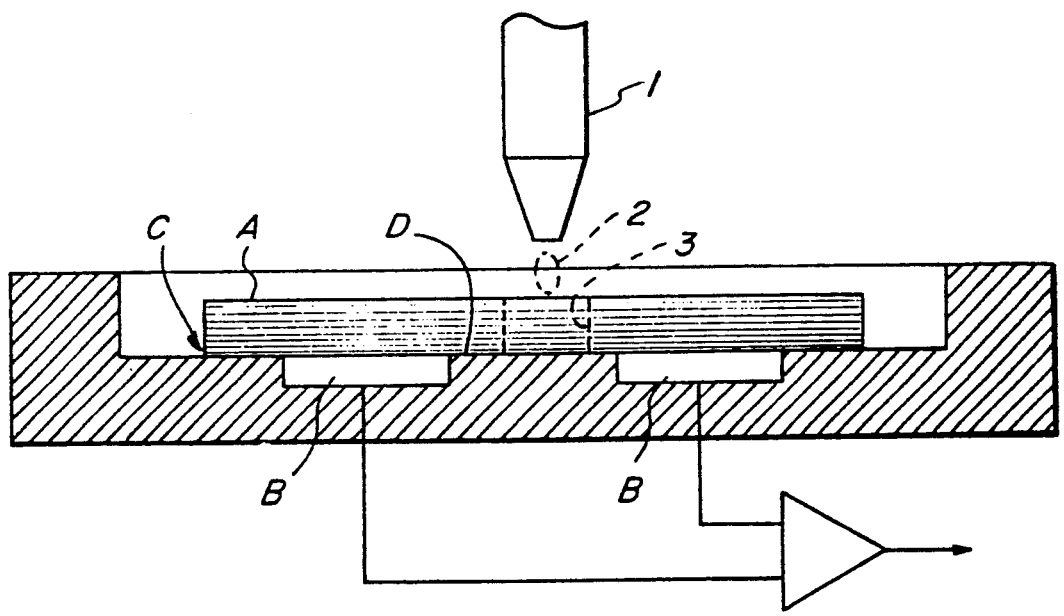
FIG. 5(A) and FIG. 5(B) are a general diagrammatical longitudinal, sectional view and a partially enlarged view thereof, respectively, showing a fourth preferred embodiment.
Figure 5B:
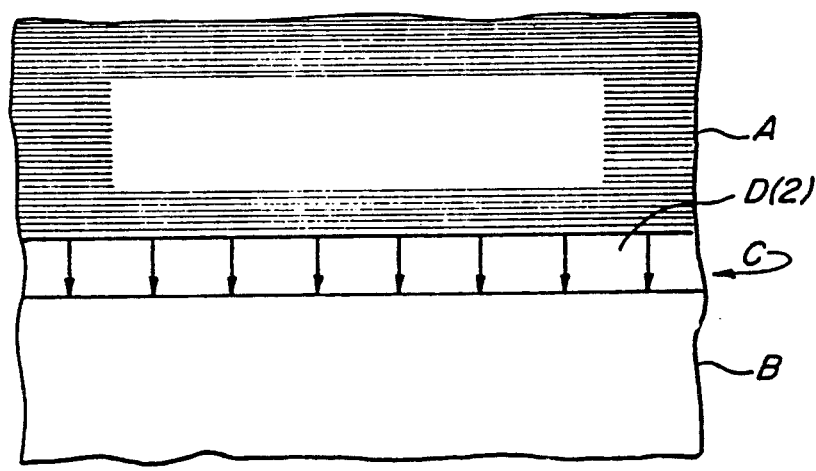

As shown in FIG. 5(A), (b), a solid body A is provided with through holes 3 or constructed from a porous body so that a liquid object 2 to be measured can be transmitted or passed therethrough, and is formed of a material which chemically or physically acts upon the liquid object 2 to be measured. At first, the solid body A is positioned so as to be substantially brought into close contact with a surface of electrodes B, $B^1$ and then the liquid object 2 to be measured is given drop by drop onto a surface of the solid body A by means of a micropipette 1 and the like to transmit or pass the liquid object 2 to be measured through the solid body A and diffuse the liquid object 2 to be measured all over a remarkably small gap C formed between the solid body A and the surface of the electrodes B, $B^1$ by its own interfacial tension. Disposing a super-thin liquid membrane D between the solid body A and the surface of the electrodes B, $B^1$ enables detection of an electric signal due to a chemical or physical reaction, which is generated by a mutual reaction of a reactive substance composing the solid body A and the liquid object 2 composing the super-thin liquid membrane D. The reaction is on an interface between the solid body A and the super-thin liquid membrane D and the reaction is diffused through the super-thin liquid membrane D. The electric signal is measured by means of the electrodes B, $B^1$, which is a measurement of the physical property of the liquid object 2 to be measured, as schematically shown by an arrow in FIG. 5(A).

Also in this fourth EXAMPLE, in order to dispose the super-thin liquid membrane D within the remarkably small gap C formed between the solid body A and the surface of the electrodes B, $B^1$, the same modification as in the first EXAMPLE may be adopted.

FIFTH EXAMPLE

Figure 6A:
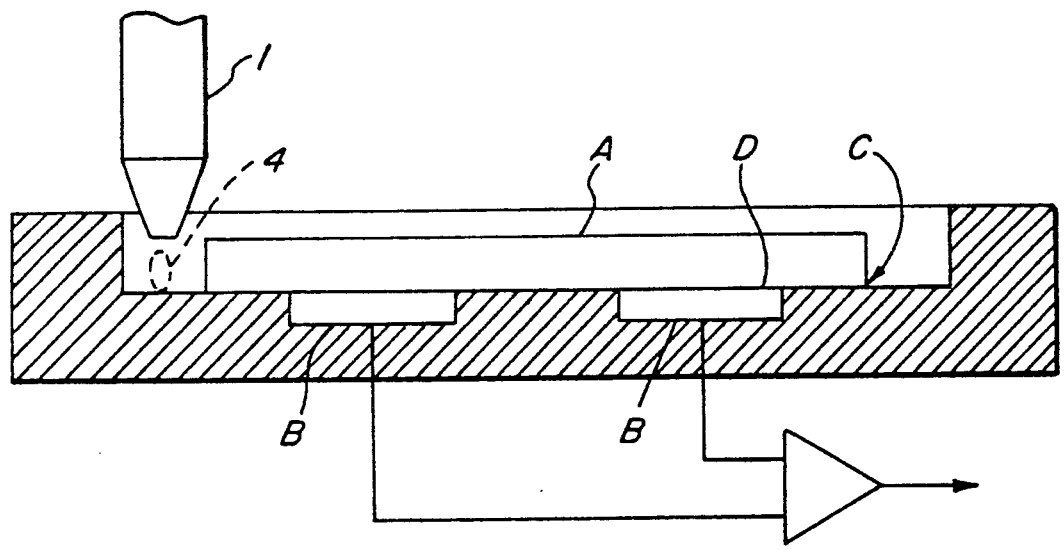
FIG. 6(A) and FIG. 6(B) are a general diagrammatical longitudinal, sectional view and a partially enlarged view thereof, respectively, showing a fifth preferred embodiment.
Figure 6B:
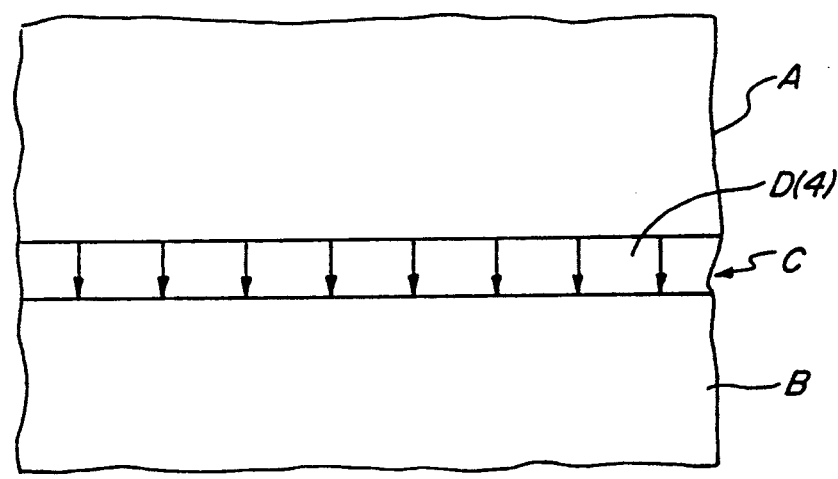

As shown in FIG. 6(A), (b), a solid object to be measured (for example, an alkali glass plate and the like) is used as a solid body A. At first, the solid body A is positioned to be substantially brought into close contact with a surface of electrodes B, $B^1$ in the same manner as in the first EXAMPLE. A liquid reactive substance 4, which chemically or physically acts upon an object to be measured and composes the solid body A (for example, pure water for eluting ions, a solution containing a special chemically reactive substance such as enzyme, or the like: a remarkably small amount of liquid reactive substance is sufficient also in this case) is given drop by drop onto the vicinity of a circumferential portion of a contact surface of the solid body A and the surface of the electrodes B, $B^1$ to spread and diffuse the liquid reactive substance 4 all over a remarkably small gap C formed between the solid body A and the surface of the electrodes B, $B^1$ by its own interfacial tension. A super-thin liquid membrane D is between the solid body A and the surface of the electrodes B, $B^1$ to detect an electric signal due to a chemical or physical reaction, which is generated by a mutual reaction of the object to be measured composing the solid body A and the liquid reactive substance 4 composing the super-thin liquid membrane D and which is diffused through the super-thin liquid membrane D itself. The reaction is on an interface of the solid body A and the super-thin liquid membrane D to enable measurement by means of the electrodes B, $B^1$ and thus measurement of the physical property (for example, a concentration of ions eluted and the like) of the object to be measured composing the solid body A, as shown by an arrow in FIG. 6(B).

Also in this fifth EXAMPLE, in order to dispose the super-thin liquid membrane D formed of the liquid reactive substance 4 within the remarkably small gap C formed between said solid body A and the surface of the electrodes B, $B^1$, the same modification as in the first EXAMPLE may be adopted.

SIXTH EXAMPLE

Figure 7A:
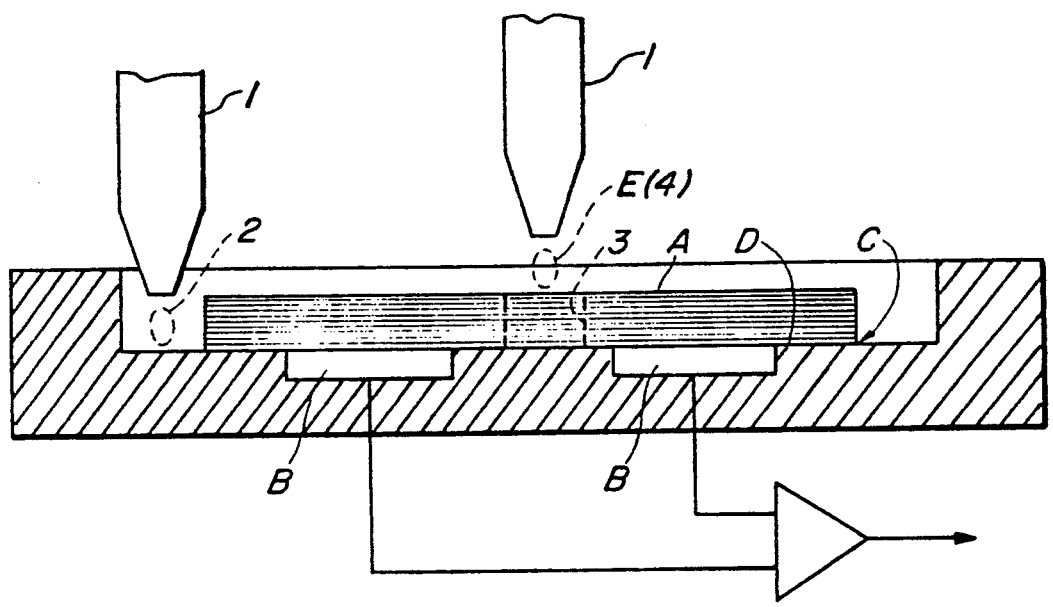
FIG. 7(A) FIG. 7(B) are a general diagrammatical longitudinal, sectional view and a partially enlarged view thereof, respectively, showing a sixth preferred embodiment.
Figure 7B:
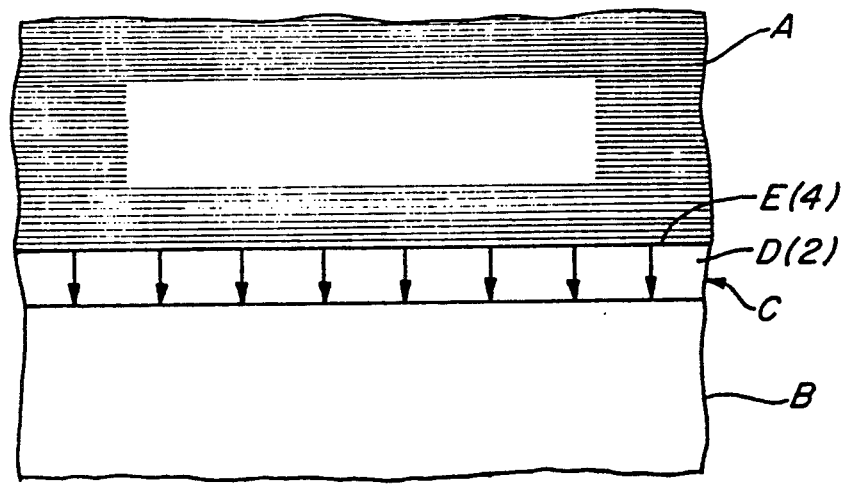

As shown in FIG. 7(B), (B), a solid body A is provided with through holes 3 or is formed of a porous body and the like so as to transmit or pass therethrough a liquid reactive substance 4 as a reactive substance E, which chemically or physically acts upon a liquid object 2 to be measured, and is formed of a substance which does not chemically or physically act upon both the liquid object 2 to be measured and the liquid reactive substance 4. At first, the solid body A is positioned so as to be substantially brought into close contact with the surface of the electrodes B, $B^1$, and then the liquid object 2 to be measured is put onto a circumferential portion of a contact surface of the solid body A and the surface of the electrodes B, $B^1$ drop by drop by means of a micropipette 1 and the like to spread and diffuse the liquid object 2 to be measured all over a remarkably small gap C formed between the solid body A and the surface of the electrodes B, $B^1$ by its own interfacial tension, whereby a super-thin liquid membrane D is disposed between the solid body A and the surface of the electrodes B, $B^1$. Subsequently, the liquid reactive substance 4 is placed drop by drop onto a surface of the solid body A by means of the micropipette 1 and the like to transmit or pass the liquid reactive substance 4 through the solid body A and spread and diffuse the liquid reactive substance 4 all over an interface of the solid body A and the liquid object 2 to be measured. Detecting an electrical signal due to a chemical or physical reaction, which is generated by a mutual reaction of the liquid reactive substance 4 and the liquid object 2 to be measured composing said super-thin liquid membrane D and which is diffused through the super-thin liquid membrane D itself, is made by means of the electrodes B, $B^1$, as schematically shown by an arrow in FIG. 7(B), and thus measurement of the physical property of the liquid object 2 to be measured is accomplished.

Also in this sixth EXAMPLE, in order to dispose the super-thin liquid membrane D formed of the liquid object 2 to be measured within the remarkably small gap C formed between the solid body A and the surface of the electrodes B, $B^1$, the same modification as in the first EXAMPLE may be adopted.

SEVENTH EXAMPLE

Figure 8A:
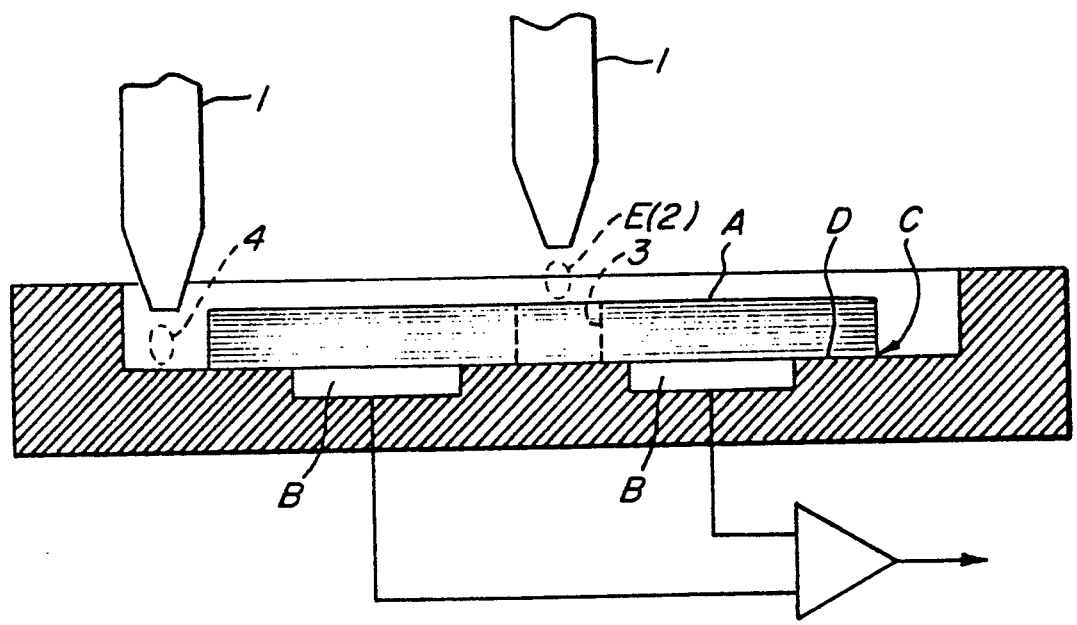
Figure 8B:
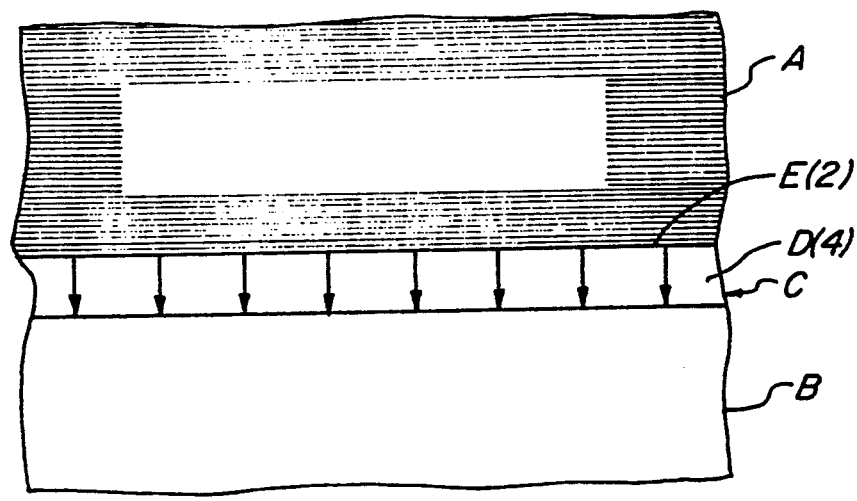

As shown in FIG. 8(A), (B), a solid body A is provided with through holes 3 or is formed of a porous body and the like so as to transmit or pass therethrough a liquid object 2 to be measured as a reactive substance E and is formed of a substance, which does not chemically or physically act upon both the liquid object 2 to be measured and the liquid reactive substance 4 used for the liquid object 2 to be measured. At first, the solid body A is positioned so as to be substantially brought into close contact with a surface of the electrodes B, $B^1$, and then the liquid reactive substance 4 is placed drop by drop onto a circumferential portion of a contact surface of the solid body A and the surface of the electrodes B, $B^1$ by means of a micropipette 1 and the like to spread and diffuse the liquid reactive substance 4 all over a remarkably small gap C formed between the solid body A and the surface of the electrodes B, B by its own interfacial tension, whereby a super-thin liquid membrane D is disposed between the solid body A and the surface of the electrodes B, $B^1$. Subsequently, the liquid object 2 to be measured is placed drop by drop onto a surface of the solid body A by means of the micropipette 1 and the like to transmit or pass the liquid object 2 to be measured through the solid body A and spread and diffuse the liquid object 2 to be measured all over an interface between the solid body A and the liquid reactive substance 4 by its own interfacial tension. An electric signal due to a chemical or physical reaction is generated by a mutual reaction of the liquid object 2 to be measured and the liquid reactive substance 4 composing the super-thin liquid membrane D and is diffused through the super-thin liquid membrane 4 itself, on an interface of the solid body A and the super-thin liquid membrane D. The electric signal is detected by means of the electrodes B, $B^1$, and thus measurement of the physical property of the liquid object 2 to be measured is accomplished, as shown by an arrow in FIG. 8(B).

Also in this seventh EXAMPLE, in order to dispose the super-thin liquid membrane D formed of the liquid reactive substance 4 within the remarkably small gap C formed between the solid body A and the surface of the electrodes B, $B^1$, the same modification as in the first EXAMPLE may be adopted.

EIGHTH EXAMPLE

Figure 9A:
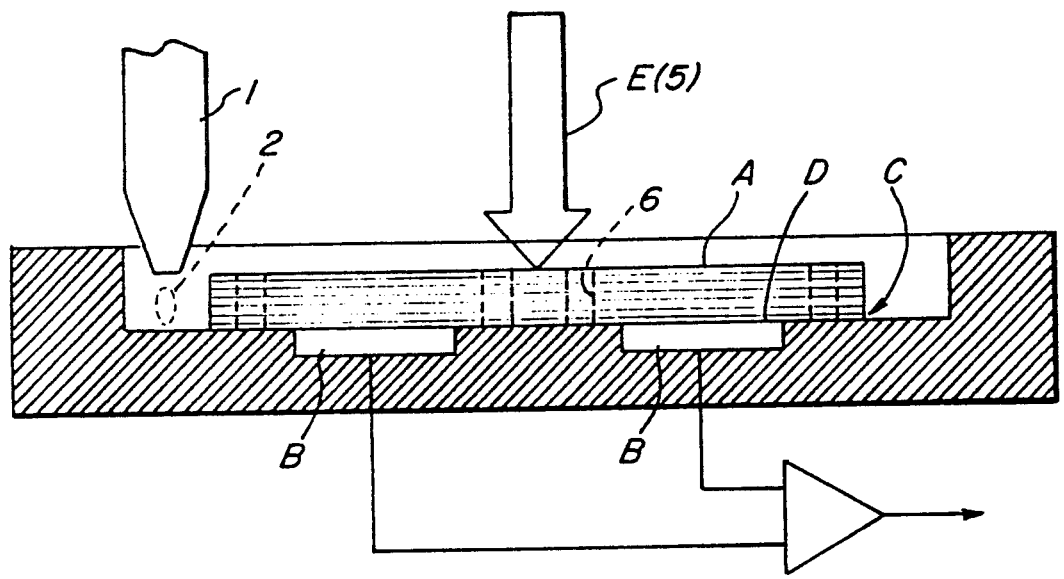
FIG. 9(A) and FIG. 9(B) are a general diagrammatical longitudinal, sectional view and a partially enlarged view thereof, respectively, showing an eighth preferred embodiment.
Figure 9B:
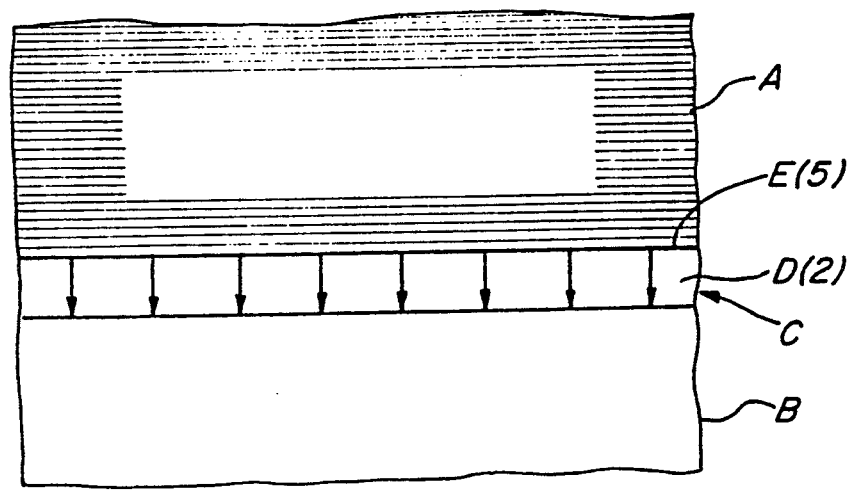

As shown in FIG. 9(A), (B), a solid body A is provided with vent holes 6 or is formed of a porous body, and is selectively permeable to gases and the like so as to transmit or pass a gaseous reactive substance 5 (for example, water vapor or gas containing a reactive gas) as a reactive substance E which chemically or physically acts upon a liquid object 2 to be measured, and is formed of a substance which does not chemically or physically act upon both the liquid object 2 to be measured and the gaseous reactive substance 5. At first, the solid body A is positioned so as to be substantially brought into close contact with a surface of electrodes B, $B^1$, and then the liquid object 2 to be measured is placed drop by drop onto a circumferential portion of a contact surface of the solid body A and the surface of the electrodes B, $B^1$ by means of a micropipette 1 and the like to spread and diffuse the liquid object 2 to be measured all over a remarkably small gap C formed between the solid body A and the surface of the electrodes B, $B^1$ by its own interfacial tension, whereby a super-thin liquid membrane D is disposed between the solid body A and the surface of the electrodes B, $B^1$. Subsequently, the gaseous reactive substance 5 is acted all over an interface of the solid body A and the liquid object 2 to be measured composing the super-thin liquid membrane D by forming a chamber, passage or the like for introducing a gas (not shown) above the solid body A, applying the gaseous reactive substance 5 to a surface of the solid body A, or flowing the gaseous reactive substance 5 on the surface of the solid body A, so as to transmit or pass the gaseous reactive substance 5 through the solid body A. An electric signal due to a chemical or physical reaction is generated by a mutual reaction of the gaseous reactive substance 5 and the liquid object 2 to be measured composing the super-thin liquid membrane D on an interface of the solid body A and the super-thin liquid membrane D and is diffused through the super-thin liquid membrane D itself. The signal is detected by means of the electrodes B, $B^1$, and thus measurement of the physical property of the liquid object 2 to be measured is accomplished.

Also in this eighth EXAMPLE, in order to dispose the super-thin liquid membrane D formed of the liquid object 2 to be measured within the remarkably small gap C formed between the solid body A and the surface of the electrodes B, $B^1$, the same modification as in the first EXAMPLE may be adopted.

NINTH EXAMPLE

Figure 10A:
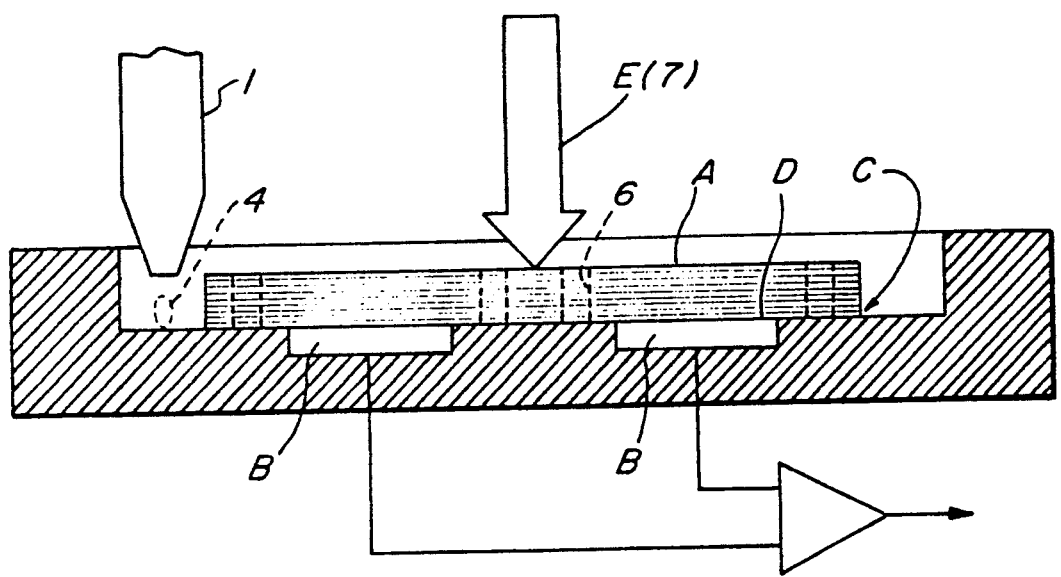
FIG. 10(A) and FIG. 10(B) are a general diagrammatical longitudinal, sectional view and a partially enlarged view thereof, respectively, showing a ninth preferred embodiment.
Figure 10B:
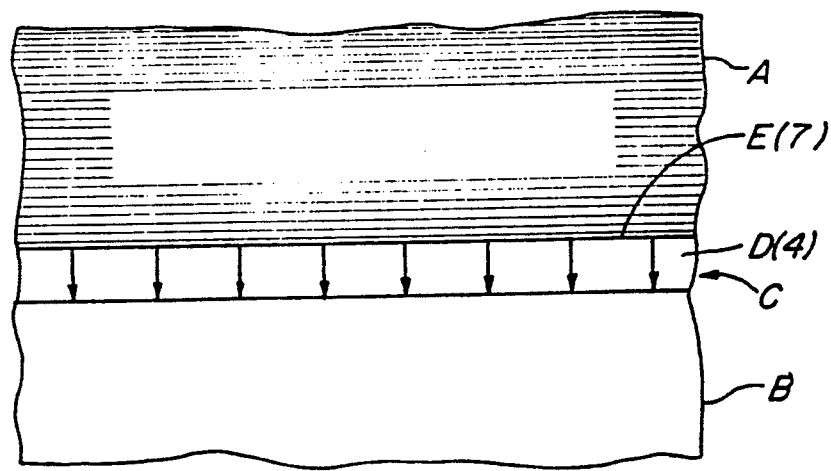

As shown in FIG. 10(A), (B), a solid body A is provided with vent holes 6 or is formed of a porous body selectively permeable to gases and the like so as to transmit or pass therethrough a gaseous object 7 to be measured as a reactive substance E, and is formed of a substance which does not chemically or physically act upon both the gaseous object 7 to be measured and a liquid reactive substance 4 used for the gaseous object 7 to be measured. At first, the solid body A is positioned so as to be substantially brought into close contact with a surface of electrodes B, $B^1$, and then the liquid reactive substance 4 is placed drop by drop onto a circumferential portion of a contact surface of the solid body A and the surface of the electrodes B, $B^1$ by means of a micropipette 1 and the like to spread and diffuse the liquid reactive substance 4 all over a remarkably small gap C formed between the solid body A and the surface of the electrodes B, $B^1$ by its own interfacial tension, whereby a super-thin liquid membrane D is disposed between the solid body A and the surface of the electrodes B, $B^1$. Subsequently, the gaseous object 7 to be measured is acted all over an interface of the solid body A and the liquid reactive substance 4 composing the super-thin liquid membrane D by, for example, forming a chamber, passage and the like (not shown) for introducing a gas above the solid body A, applying the gaseous object 7 to be measured to a surface of the solid body A or flowing the gaseous object 7 to be measured on the surface of the solid body A, to transmit or pass the gaseous object 7 to be measured through the solid body A. Thereby, the gaseous object 7 to be measured is acted all over the interface of the solid body A and the liquid reactive substance 4 composing the super-thin liquid membrane D. An electric signal due to a chemical or physical reaction is generated by a mutual reaction of the gaseous object 7 to be measured and the liquid reactive substance 4 composing the super-thin liquid membrane D and is diffused through the super-thin liquid membrane D itself on the interface of the solid body A and the super-thin liquid membrane D. The signal is detected by means of the electrodes B, $B^1$, and thus measurement of the physical property of the gaseous object 7 to be measured, as schematically shown by an arrow in FIG. 10(B) is accomplished.

Also in this ninth EXAMPLE, in order to dispose the super-thin liquid membrane D formed of the liquid reactive substance 4 within the remarkably small gap C formed between the solid body A and the surface of the electrodes B, $B^1$, the same modification as in the first EXAMPLE may be adopted.

TENTH EXAMPLE

Figure 11A:
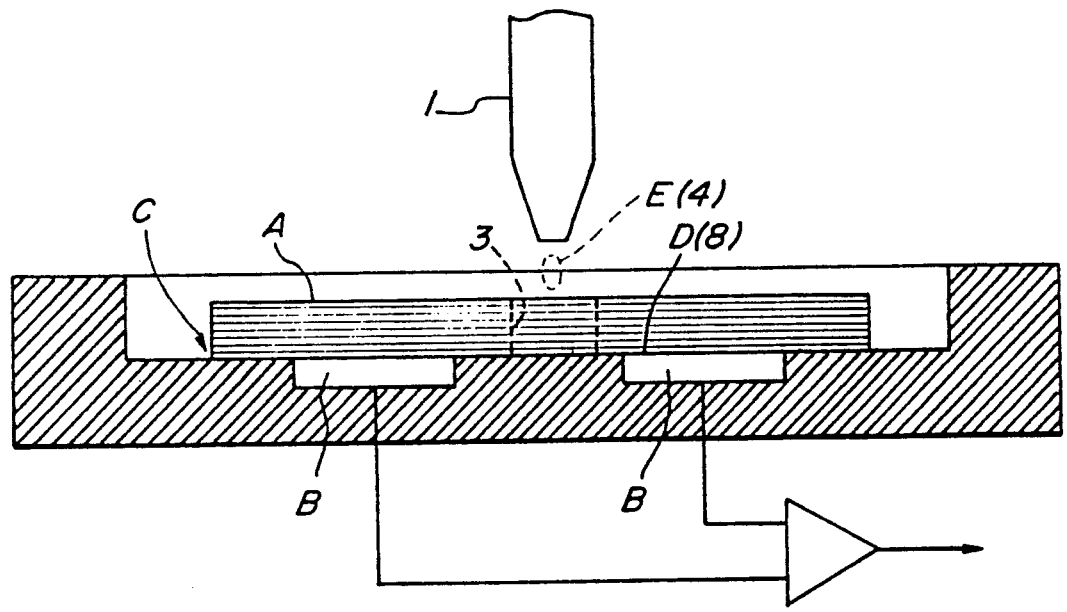
FIG. 11(A) and FIG. 11(B) are a general diagrammatical longitudinal, sectional view and a partially enlarged view thereof, respectively, showing a tenth preferred embodiment.
Figure 11B:
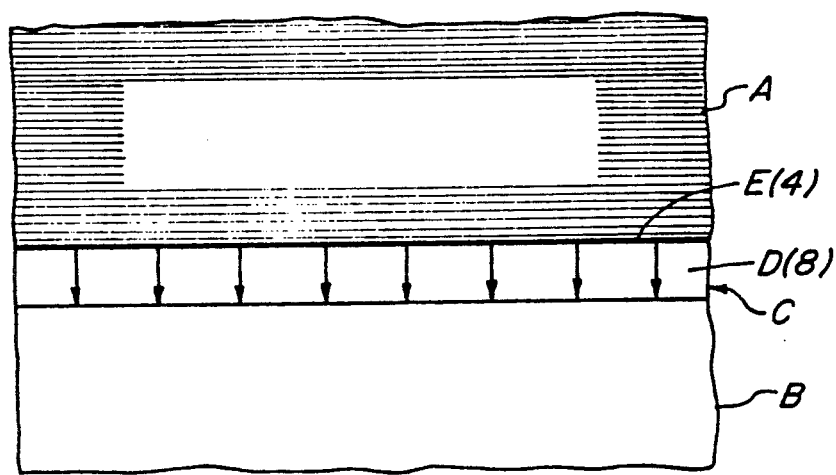

As shown in FIG. 11(A), (B), a solid body A is provided with through holes 3 or is formed of a porous body and the like so as to be capable of transmitting or passing therethrough a liquid reactive substance 4 as a reactive substance E, which chemically or physically acts upon a super-thin solid membrane object 8 to be measured, which will be mentioned later, and is formed of a substance which does not act upon both the super-thin solid membrane object 8 to be measured and the liquid reactive substance 4. At first, the super-thin solid membrane object 8 to be measured (this may be powdery) is formed in a remarkably thin membrane and has a property of being capable of spreading the liquid reactive substance 4 all over thereon or dissolving to turn into a solution by the action of the liquid reactive substance 4. The membrane object is placed on a surface of electrodes B, $B^1$ and then the solid body A is placed on the super-thin solid membrane object 8 to be measured. This is followed by placing the liquid reactive substance 4 drop by drop onto a surface of the solid body A to transmit or pass the liquid reactive substance 4 through the solid body A and spread and diffuse the liquid reactive substance 4 all over an interface of the solid body A and the super-thin solid membrane object 8 to be measured. Spreading the liquid reactive substance 4 all over the super-thin solid membrane object 8 to be measured or turning the super-thin solid membrane object 8 to be measured into a solution to dispose a super-thin liquid membrane D between the solid body A and the surface of the electrodes B, $B^1$ provides an electric signal due to a chemical or physical reaction, which is generated by a mutual reaction of the liquid reactive substance 4 composing the super-thin liquid membrane D and the super-thin solid membrane object 8 to be measured on an interface of the solid body A and the super-thin liquid membrane D and which is diffused through the super-thin liquid membrane D itself, as schematically shown by an arrow in FIG. 11(B). The signal is detected by means of the electrodes B, $B^1$ to measure the physical property of the super-thin solid membrane object 8 to be measured.

ELEVENTH EXAMPLE

Figure 12A:
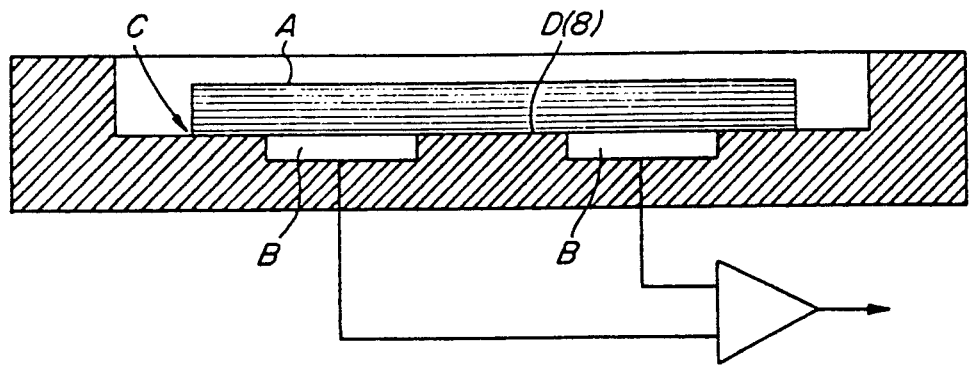
FIG. 12(A) and FIG. 12(B) are a general diagrammatical longitudinal, sectional view and a partially enlarged view thereof, respectively, showing a eleventh preferred embodiment.
Figure 12B:
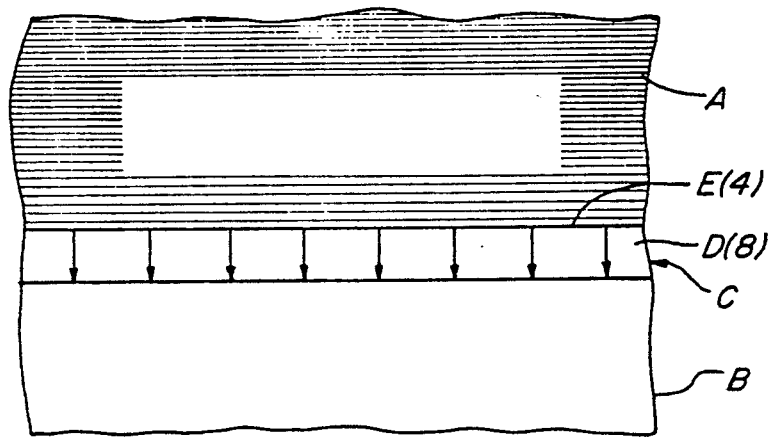
Figure 13:
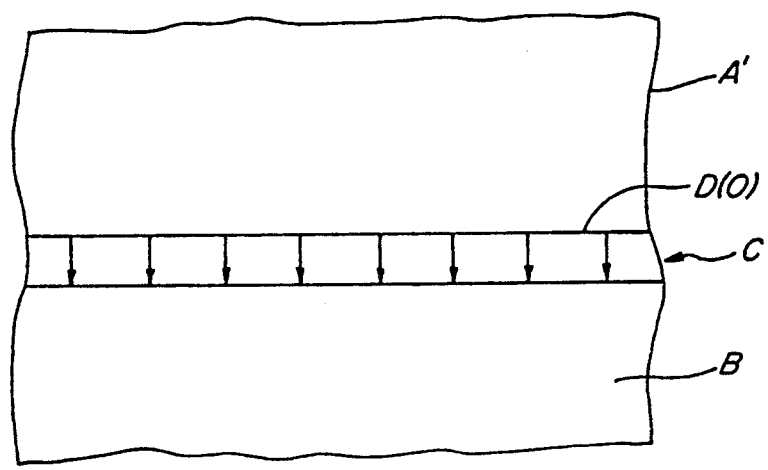
FIG. 13 is a partially enlarged view for describing mainly the operation of an interface reaction detection type biosensor by a super-thin liquid membrane forming mode according to the present invention.

As shown in FIG. 12(A), (B), a solid body A is adapted to ooze out a liquid reactive substance 4, and can be an absorbent body or gelatinized body previously impregnated with the liquid reactive substance 4 as a reactive substance E which chemically or physically acts upon a super-thin solid membrane object 8 to be measured which will be mentioned later, and is formed of a substance which does not chemically or physically act upon both the super-thin solid membrane object 8 to be measured and the liquid reactive substance 4. The super-thin solid membrane object 8 to be measured (this may be powdery) is formed in a remarkably thin membrane and has a property of being capable of spreading the liquid reactive substance 4 all over thereon or dissolving to turn into a solution by the action of the liquid reactive substance 4. The membrane object is placed on a surface of electrodes B, $B^1$ and then the solid body A is placed on the super-thin solid membrane object 8 to be measured followed by spreading and diffusing the liquid reactive substance 4 oozed out of the solid body A all over an interface of the solid body A and the super-thin solid membrane object 8 to be measured by its own interfacial tension to spread the liquid reactive substance 4 all over the super-thin solid membrane object 8 to be measured or turn the super-thin solid membrane object 8 to be measured into a solution. Disposing a super-thin liquid membrane D between the solid body A and the surface of the electrodes B, $B^1$ allows detection by means of said electrodes B, $B^1$ of an electric signal due to a chemical or physical reaction, which is generated by a mutual reaction of the liquid reactive substance 4 composing the super-thin liquid membrane D and the super-thin solid membrane object 8 to be measured on an interface of the solid body A and the super-thin liquid membrane D and diffused through the super-thin liquid membrane D itself, as schematically shown by an arrow in FIG. 12(B). Thus, measurement of the physical property of the super-thin solid membrane object 8 to be measured is accomplished.

In the formation of the super-thin liquid membrane D according to the above-described EXAMPLES, there is a tendency that the sensitivity of measurement and response speed is improved with a decrease of the thickness. Thus, with the present invention, it can be said that merely a remarkably small amount of the liquid object 2 to be measured, liquid reactive substance 4, super-thin solid membrane (powdery) substance 8 to be measured and the like, which are constituent elements of the super-thin liquid membrane D, is not only sufficient, but a remarkably small amount of them is preferably used.

In addition, it is desirable to use electrodes B, $B^1$, whose surfaces (detecting surfaces) are formed as flat as possible, in the above-described EXAMPLES. A sheet-type sample electrode, which has already been developed and proposed by Horiba, Ltd., can be very suitably used for this (refer to Japanese Utility Model Application No. 97385/1985, Japanese patent application No. 285371/1986, Japanese patent application No. 286269/1986, Japanese Utility Model Application No. 191498/1986 and many others).

Various kinds of electrodes, such as ion-selective electrodes, reference electrodes, dissolved oxygen-measuring electrodes, conductivity-measuring electrodes, oxidation-reduction electrodes and bioelectrodes, can be used singly or in combination, that is, in the form of composite electrodes, as the electrodes B, $B^1$. Accordingly, various kinds of physical properties of the object to be measured can be measured.

Next, an interface reaction detection type biosensor by a super-thin liquid membrane forming mode according to a second embodiment of the present invention is described.

TWELFTH EXAMPLE

As shown in FIG. 14, electrodes B, $B^1$ (i.e., electrodes of a kind corresponding to a particular physical property to be measured is selected) having a flat response surface is embedded in a flat bottom portion of a concave portion 11 of a sheet substrate member 12 provided with the concave portion 11 formed on an upper surface side thereof. Thereby, a living body reactive membrane A' (for example, an enzyme-fixed membrane, antibody-fixed membrane, antigen-fixed membrane and the like), which biologically acts upon an object solution to be measured, may be placed so as to be brought into close contact with the electrodes B, $B^1$, and a space S is formed so that the object solution O to be measured may be placed drop by drop onto a circumference of the living body reactive membrane A' under the condition that the living body reactive membrane A' is placed on the electrodes B, B¹. That is to say, in the interface reaction detection type biosensor having such construction, at first, the living body reactive membrane A' is positioned on the electrodes B, B¹ on the bottom portion within the concave portion 11 of the substrate member 12 so as to be substantially brought into close contact with the response surface of the electrodes B, B¹. The object solution O to be measured is then placed drop by drop in the space S formed in the vicinity of the circumference of a contact surface of the living body reactive membrane A' and the response surface of the electrodes B, B¹ by means of a micropipette 1 and the like (a remarkably small amount of the object solution O to be measured of, for example, several microliters). This diffuses the object solution O to be measured all over a remarkably small gap C formed between the living body reactive membrane A' and the surface of the electrodes B, B¹ by its own interfacial tension, whereby a super-thin liquid membrane D is disposed between the living body reactive membrane A' and the response surface of the electrodes B, B¹. Thus, an electric signal due to a living body reaction, which is generated by a mutual reaction of the living body reactive membrane A' and the super-thin liquid membrane D and diffused through the super-thin liquid membrane D itself, is detected by the electrodes B, B¹ on the interface of the living body reactive membrane A' and the super-thin liquid membrane D to measure the physical property of the object solution O to be measured.

In addition, although in the above-described twelfth EXAMPLE, in order to dispose the super-thin liquid membrane D formed of the object solution O to be measured within the remarkably small gap C formed between the living body reactive membrane A' and the surface of the electrodes B, B¹, the living body reactive membrane A' was first positioned so as to be substantially brought into close contact with the response surface of the electrodes B, B¹, and then the object solution O to be measured was placed drop by drop into the space S formed on the circumference of the living body reactive membrane A' to transmit and diffuse the object solution O to be measured all over the remarkably small gap C by its own interfacial tension, the following procedure may be adopted:

At first, the object solution O to be measured may be placed drop by drop onto an almost central portion of the bottom in the concave portion 11 of the substrate member 12 or the response surface of the electrodes B, B¹. Then, the living body reactive membrane A' may be positioned so as to be substantially brought into close contact with the response surface of the electrodes B, B and putting the object solution O to be measured given drop by drop between the living body reactive membrane A' and the response surface of the electrodes B, B¹ (by merely placing the living body reactive membrane A' on the electrodes B, B¹, or placing the living body reactive membrane A' on the electrodes and then giving some pressing force, and the like). That diffuses the object solution O to be measured all over the remarkably small gap C formed between the living body reactive membrane A' and the response surface of the electrodes B, B¹ by its own interfacial tension. Thus, it is not required to specially form the space S for placing the object solution O to be measured therein.

THIRTEENTH EXAMPLE

As shown in FIG. 15, a living body reactive membrane A' is provided with through holes 13 to transmit or pass therethrough an object solution O to be measured or is formed of a porous body and the like. The living body reactive membrane A' is adapted to be able to be placed on electrodes B, B¹ in a bottom within a concave portion 11 of a substrate member 12 so as to be substantially brought into close contact with a response surface of the electrodes B, B¹. At first, the living body reactive membrane A' is positioned on the electrodes B, B¹ so as to be substantially brought into close contact with the response surface of the electrodes B, B¹. The object solution O to be measured is then placed onto the living body reactive member A' drop by drop by means of a micropipette 1 and the like to transmit or pass the object solution O to be measured through the living body reactive membrane A' and diffuse the object solution O to be measured all over the remarkably small gap C formed between the living body reactive membrane A' and the surface of the electrodes B, B¹ by its own interfacial tension, whereby a super-thin liquid membrane D is disposed between the living body reactive membrane A' and the response surface of the electrodes B, B¹. Thus, an electric signal due to a living body reaction, which is generated by a mutual reaction of the living body reactive member A' and the object solution O to be measured composing the super-thin liquid membrane D and which is diffused through the super-thin liquid membrane D itself, is detected by the electrodes B, B¹ to measure the physical property of the object solution O to be measured in the same manner as in the above-described twelfth EXAMPLE.

Also in this thirteenth EXAMPLE, it is not required to specially form a space S for giving the object solution O to be measured in a dropwise fashion, as in the twelfth EXAMPLE.

FOURTEENTH EXAMPLE

As shown in FIG. 16, a sheet substrate member 12 having a concave portion 11 formed on an upper surface side thereof is provided with a cover member 15 having on a lower surface side thereof a projection member 14 engaged with the concave portion 11 of the substrate member 12 so as to be swung and opened and closed around a side axis shaft line X of one side edge portion thereof. Electrodes B, B¹ are provided on a side of a bottom (inside surface portion) of the concave portion 11 of the substrate member 12. A living body reactive membrane A' is detachably provided on the side of the lower surface portion (inside surface portion) of the projection member 14 of the cover member 15, whereby the living body reactive membrane A' is substantially brought into close contact with the electrodes B, B¹ when the cover member 15 is closed.

In this case, at first the appointed living body reactive membrane A' is mounted on the lower surface portion of the projection member 14 when the cover member 15 is opened. An object solution O to be measured is then placed drop by drop onto an almost central portion of a bottom within the concave portion 11 of the substrate member 12 or a response surface of the electrodes B, B¹ by means of a micropipette 1 (not shown) and the like. Subsequently, if the cover member 15 is closed, the living body reactive membrane A' is positioned on the electrodes B, B¹ so as to be brought into close contact with the electrodes B, B¹ and pressed against the response surface. Thereby, the object solution O to be measured is diffused all over an inside of a remarkably small gap (not shown) formed between the living body reactive membrane A' and the response surface of the electrodes B, B¹ by its own interfacial tension to form a super-thin liquid membrane (not shown) between the living body reactive membrane A' and the response surface of the electrodes B, B¹. Accordingly, the physical property of the object solution O to be measured is measured in the same manner as in the twelfth EXAMPLE.

FIFTEENTH EXAMPLE

This EXAMPLE is a modification of the above-described fourteenth EXAMPLE. As shown in FIG. 17, a substrate member 12 and a cover member 15 are separately formed and the cover member 15 is detachably mounted on the substrate member 12.

Other constructions, operations and the like are the same as in the above-described fourteenth EXAMPLE, so that members having the same functions are marked with the same reference numerals and marks and therefore their descriptions are omitted.

SIXTEENTH EXAMPLE

This EXAMPLE is a modification of the fourteenth EXAMPLE. As shown in FIG. 18, a substrate member 12 is detachably provided with a living body reactive membrane A' on a side of a bottom (inside surface portion) in a concave portion 11 thereof, and electrodes B, B¹ are provided on a side of a lower surface portion (inside surface portion) of a projection member 14 of a cover member 15. Accordingly, in this case, at first an appointed living body reactive membrane A' is mounted on the bottom in the concave portion 11 of the substrate member 12 when the cover member 15 is opened. An object solution O to be measured is then placed onto the living body reactive membrane A' drop by drop by means of a micropipette (not shown) and the like, and then the cover member 15 is closed to position the response surface of the electrodes B, B¹ on the living body reactive membrane A' so as to be brought into close contact with and pressed against the living body reactive membrane A' under the condition that the object solution O to be measured is put between the response surface of the electrodes B, B¹ and the living body reactive membrane A' so that the physical property of the object solution O to be measured is measured in the same manner as in the fourteenth EXAMPLE.

In the above-described EXAMPLES, there is a tendency that the sensitivity of measurement and the response speed are improved with a decrease in thickness of the super-thin liquid membrane in the formation of the super-thin liquid membrane. Therefore, in the case of the present invention, it can be said that a remarkably small amount of the liquid object to be measured, liquid reactive substance, super-thin solid membrane (powdery) substance to be measured and the like, which are constituent elements of the super-thin liquid membrane, are required and a remarkably small amount of them is preferably used.

In addition, it is desirable to use the electrodes B, B¹ whose response surfaces are formed as highly flat as possible in the above-described EXAMPLES. To this end, a sheet-type sample electrode, which has already been developed and proposed by Horiba, Ltd. (refer to, for example, U.S. Pat. No. 4,797,188, U.S. Pat. No. 4,816,132 Japanese Utility Model Application No. 97385/1985, Japanese patent application No. 285371/1986, Japanese patent application No. 286269/1986, Japanese Utility Model Application No. 191498/1986 and many others) can be very suitably used.

In addition, various kinds of electrodes, such as ion-selective electrodes, reference electrodes, dissolved oxygen-measuring electrodes, conductivity-measuring electrodes and oxidation-reduction electrodes, can be used singly or in combination as the electrodes B, B. Accordingly, various kinds of physical properties of the object to be measured can be measured.

FIG. 19 shows one EXAMPLE of the electrodes B, B, and this is an example to which the thirteenth EXAMPLE (FIG. 15) is applied.

In this case, electrodes B, B¹ are provided with an ion-selective electrode 19 (for example, a pH-electrode) comprising an ion-selective response membrane 16, a gelatinized internal solution 17 and a silver chloride electrode 18 and with a reference electrode 22 comprising a silver chloride electrode brought into contact with a gelatinized internal solution 21 provided with a liquid junction 20 exposed on a bottom of a concave portion 11 of a substrate member 12. In addition, a living body reactive membrane A' comprising a vaporization-preventing membrane 24 stuck to an upper surface side of an enzyme-fixed membrane 23, on which an enzyme (for example, glucose oxydase) is fixedly mounted, is used. For example, in the case where a concentration of $\beta$-D-glucopyranose contained in an object solution O to be measured is measured, the pH of gluconic acid, which is formed by a living body reaction of a super-thin liquid membrane D formed of the object solution O to be measured and the living body reactive membrane A', is measured.

Other fundamental constructions, operations and the like are the same as in the thirteenth EXAMPLE, so that the members having the same functions are marked with the same reference numerals and marks and their descriptions are omitted.

As is obvious from the above-described detailed description, the method of measuring physical properties by a super-thin liquid membrane forming mode according to the present invention is a method using a remarkably small amount of sample in comparison with the conventional and prior art and exhibits a remarkably superior effect in that the physical property of the object to be measured can be surely, directly and very efficiently measured by a simple operation in a short time without requiring any troublesome pretreatment, such as the previous liquefaction, regardless of the liquid object to be measured, the solid object to be measured or the gaseous object to be measured, even though merely a remarkably small amount of sample can be obtained.

In addition, with the interface reaction detection type biosensor by a super-thin liquid membrane forming mode according to the present invention, the living body reactive membrane biologically acts upon the object solution to be measured and is disposed so as to be substantially brought into close contact with the electrodes or capable of bringing into close contact with the electrodes and the super-thin liquid membrane formed of the object solution to be measured is adapted to be disposed within the remarkably small gap formed between the living body reactive membrane and the electrodes utilizing the interfacial tension of the object solution to be measured itself, so that a superior effect can be exhibited in that the physical property of the object to be measured can be surely and very efficiently measured by an easy operation in a short time even though merely a remarkably small amount of sample ca be obtained.

What is claimed is:

1. In a method of measuring a physical property of a specimen through the use of electrodes, the improvement comprising the steps of:
   providing a support structure for the electrodes;
   disposing a member across the electrodes to form a small gap between at least portions of the member, extending across the electrodes, and the electrodes;
   forming a thin liquid buffer solution by only the use of an interfacial tension of a liquid disposed within the small gap, the member being positioned close enough to the electrodes so that the interfacial tension exists when the liquid is introduced;
   applying a specimen to be measured to one of said member and said thin liquid buffer solution wherein measurements can be made by the electrodes on a relatively small sample of a specimen, and
   performing measurements by the electrodes on a relatively small sample of a specimen.

2. A method of measuring the physical property as set forth in claim 1, wherein forming said thin liquid buffer solution membrane between said member and said surface of said electrodes is further characterized by constructing said member so as to be capable of transmitting said liquid therethrough, and said method is further characterized by first positioning said member so as to be substantially brought into close contact with said surface of the electrodes, and then placing said liquid drop by drop onto a surface of said member to transmit said liquid through said member to diffuse said liquid all over said small gap formed between said member and said surface of the electrodes by its own interfacial tension.

3. The method of measuring a physical property as set forth in claim 1, wherein the specimen is applied as a liquid in a drop-by-drop microliter application adjacent an edge of the member to contact said thin liquid material.

4. The method of measuring a physical property as set forth in claim 1, wherein the member is porous and the specimen is applied as a liquid to an external surface remote from the electrodes and is transmitted to the liquid material through the member.

5. A method of measuring physical properties as set forth in claim 1, wherein only several microliters of specimen are applied in a drop-by-drop application.

6. A biosensor detection cell comprising:
   a substrate supporting means for electrically picking up signals with electrodes;
   a living body reactive membrane having an agent that will react with a specimen to provide an electrical signal characteristic of the specimen, and
   a thin liquid material containing the specimen to be detected, positioned in a space between the electrodes and the membrane, the size of the space extending between the electrodes and the membrane defining an opening wherein an interfacial tension will cause the thin liquid material to extend across the electrodes.

7. The invention of claim 6 wherein the reactant membrane is removable.

8. The invention of claim 6 further including means for introducing the specimen adjacent one side of the reactant membrane.

9. The invention of claim 6 wherein the reactant membrane is porous and the specimen can travel through the material to enter the liquid membrane.

10. In a method of measuring a physical property of a liquid specimen through the use of electrodes, the improvement comprising:
    providing a support structure for the electrodes;
    applying a liquid specimen to be measured on only a portion of the electrodes;
    disposing a member, formed with a material that can chemically react with the specimen to provide an electrical potential that can be measured by the electrodes, the member being positioned on the liquid specimen sufficiently close enough to the electrodes to spread the liquid specimen across the entire electrodes, and
    performing measurements by the electrodes on the liquid specimen whereby a relatively small sample of a specimen can be measured.

11. A method of measuring a physical property as set forth in claim 10, wherein the liquid specimen is placed drop by drop on a portion of the electrodes.

12. A biosensor detection cell comprising:
    a substrate support means for electrically picking up signals with electrodes;
    a cover member provided above said substrate so as to be capable of opening and closing;
    a living body reactive membrane which can react with a specimen to provide an electrical signal characteristic of the specimen, mounted on the cover member and positioned to react with the specimen when the cover member is closed and the living body reactive membrane contacts the specimen, and
    means for providing an electrical signal representative of the specimen.

13. The biosensor detection cell of claim 12 wherein the reactive membrane is positioned sufficiently close to the electrodes when the cover member is closed to provide a gap of a size that a liquid specimen will be diffused over the electrodes by its own interfacial tension.

14. A biosensor detection cell comprising:
    a housing;
    a cover member connected to the housing so as to be capable of opening and closing;
    a living body reactive membrane which can react with a specimen to provide an electrical signal characteristic of the specimen, mounted in the housing and positioned to react with the specimen when the living body reactive membrane contacts the specimen;
    means for electrically detecting signals with electrodes mounted on the cover member, and
    means, connected to the electrodes, for providing an electrical signal representative of the specimen.

15. A detection cell comprising:
    a lower substrate support means for electrically detecting signals with electrodes;
    an upper porous body extending adjacent to and across the electrodes to form a small gap between at least portions of a lower surface of the porous body and the electrodes;
    means for applying a liquid sample containing a specimen to be measured in a drop-by-drop application to an exterior surface of the porous body, the porous body transmitting the liquid sample to the gap, and the gap being of such a dimension to cause interfacial tension to spread the liquid sample across the electrodes, and means, connected to the electrodes, for providing an electrical signal representative of the specimen.

16. The detection cell of claim 15 wherein the means for applying a liquid sample includes a micropipette for dispensing several microliters of liquid sample.

17. The detection cell of claim 15 wherein the upper porous body further incorporates a reactive substance that will react with the specimen to provide a characteristic electrical reaction that can be detected by the electrodes.

18. The detection cell of claim 17 wherein the upper porous body is removably mounted for replacement to enable a contaminate-free detection.

19. The detection cell of claim 18 wherein the reactive substance is a biologically reactive substance consisting of a material selected from one of an enzyme, antibody, or antigen material.

* * * * *